United States Patent
Wood et al.

(10) Patent No.: US 12,329,927 B2
(45) Date of Patent: Jun. 17, 2025

(54) MULTIPLE TELESCOPING SCREW-DRIVEN PUMP MECHANISM WITH ANTI-ROTATION OF INNERMOST SCREW KEYED TO RESERVOIR PLUNGER IN FLUID DELIVERY DEVICE

(71) Applicant: Becton, Dickinson and Company, Franklin Lakes, NJ (US)

(72) Inventors: Mark Wood, Sterling, MA (US); Dana Cote, Boxford, MA (US); Alessandro Pizzochero, Chelmsford, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 818 days.

(21) Appl. No.: 17/401,876

(22) Filed: Aug. 13, 2021

(65) Prior Publication Data

US 2022/0054740 A1 Feb. 24, 2022

Related U.S. Application Data

(60) Provisional application No. 63/066,851, filed on Aug. 18, 2020.

(51) Int. Cl.
*A61M 5/145* (2006.01)
*A61M 5/31* (2006.01)
*A61M 5/315* (2006.01)

(52) U.S. Cl.
CPC ........ *A61M 5/1452* (2013.01); *A61M 5/3129* (2013.01); *A61M 5/31511* (2013.01); *A61M 5/31528* (2013.01); *A61M 5/31535* (2013.01)

(58) Field of Classification Search
CPC .............. A61M 5/1452; A61M 5/3129; A61M 5/31511; A61M 5/31528
See application file for complete search history.

(56) References Cited

U.S. PATENT DOCUMENTS

| | | | |
|---|---|---|---|
| 5,097,122 A | | 3/1992 | Colman et al. |
| 5,647,853 A | * | 7/1997 | Feldmann ......... A61M 5/16854 604/154 |

(Continued)

FOREIGN PATENT DOCUMENTS

| | | |
|---|---|---|
| JP | 2007-502146 A | 2/2007 |
| JP | 2010-501283 A | 1/2010 |

(Continued)

*Primary Examiner* — Bradley J Osinski
(74) *Attorney, Agent, or Firm* — Dickinson Wright PLLC

(57) ABSTRACT

A fluid delivery device has a syringe barrel-type reservoir with plunger and plunger driver assembly comprising nested, telescopic screws comprising an innermost screw keyed to a first side of the plunger or intermediate pusher to prevent rotation. In a fully retracted position, the nested screws do not extend into the reservoir. The nested screws all have right handed threads and employ the same pitch in their respective inner thread and outer thread designs. The outermost screw is connected to a motor for controllable rotation. The decreasing torque ratios from the outermost to innermost screw member and anti-rotation feature allows the innermost screw to advance the plunger into the reservoir before the adjacent concentric screw member commences rotating and advancing within its corresponding screw, and so on, to translate the plunger and expel fluid in a fluid chamber defined on the other, second side of the plunger.

28 Claims, 16 Drawing Sheets

(56) References Cited

U.S. PATENT DOCUMENTS

| | | |
|---|---|---|
| 5,919,167 A | 6/1999 | Mulhauser et al. |
| 5,938,642 A | 8/1999 | Burroughs et al. |
| 6,248,093 B1 | 6/2001 | Moberg |
| 6,663,602 B2 | 12/2003 | Moller |
| 6,786,890 B2 | 9/2004 | Preuthun et al. |
| 7,063,684 B2 | 6/2006 | Moberg |
| 7,066,909 B1 | 6/2006 | Peter et al. |
| 9,022,991 B1 | 5/2015 | Moeller |
| 9,345,836 B2 | 5/2016 | Cabiri et al. |
| 9,572,927 B2 | 2/2017 | Bruggemann et al. |
| 9,656,019 B2 | 5/2017 | Cabiri et al. |
| 9,987,432 B2 | 6/2018 | Cabiri et al. |
| 10,086,145 B2 | 10/2018 | Cabiri et al. |
| 10,149,943 B2 | 12/2018 | Bar-El et al. |
| 10,149,947 B2 | 12/2018 | Bayer et al. |
| 10,159,785 B2 | 12/2018 | Cabiri |
| 10,179,204 B2 | 1/2019 | Cabiri |
| 10,251,996 B2 | 4/2019 | Bente, IV et al. |
| 10,376,647 B2 | 8/2019 | Farris et al. |
| 10,420,880 B2 | 9/2019 | Degtiar et al. |
| 2006/0206057 A1* | 9/2006 | DeRuntz ........... A61M 5/31551 604/224 |
| 2008/0077081 A1* | 3/2008 | Mounce ............ A61M 5/14248 604/67 |
| 2009/0093792 A1* | 4/2009 | Gross ................ A61M 5/31596 604/218 |
| 2009/0299290 A1 | 12/2009 | Moberg |
| 2012/0172817 A1* | 7/2012 | Bruggemann .... A61M 5/14566 604/218 |
| 2013/0245604 A1 | 9/2013 | Kouyoumjian et al. |
| 2014/0094754 A1* | 4/2014 | Servansky ........ A61M 5/14216 604/152 |
| 2014/0364808 A1 | 12/2014 | Niklaus et al. |
| 2015/0005703 A1* | 1/2015 | Hutchinson ....... A61M 5/14566 604/95.01 |
| 2016/0114109 A1 | 4/2016 | Lavi |
| 2017/0080157 A1* | 3/2017 | Cabiri ................ A61M 5/31511 |
| 2017/0112998 A1 | 4/2017 | Degtiar et al. |
| 2017/0189607 A1 | 7/2017 | Cabiri et al. |
| 2017/0246382 A1 | 8/2017 | Niklaus |
| 2017/0319788 A1 | 11/2017 | Morris et al. |
| 2018/0021521 A1 | 1/2018 | Sanchez |
| 2018/0154081 A1 | 6/2018 | Bar-El et al. |
| 2018/0250476 A1 | 9/2018 | Cabiri et al. |
| 2019/0030241 A1 | 1/2019 | Cabiri et al. |
| 2019/0091399 A1 | 3/2019 | Calasso et al. |
| 2019/0105445 A1 | 4/2019 | Bar-El et al. |
| 2019/0167899 A1 | 6/2019 | Cabiri |
| 2020/0009316 A1 | 1/2020 | Cabiri et al. |
| 2020/0023121 A1 | 1/2020 | Thomas et al. |

FOREIGN PATENT DOCUMENTS

| | | |
|---|---|---|
| JP | 2010-540156 A | 12/2010 |
| JP | 2012-516738 A | 7/2012 |
| JP | 2016-527938 A | 9/2016 |
| JP | 2018-047239 A | 3/2018 |

* cited by examiner

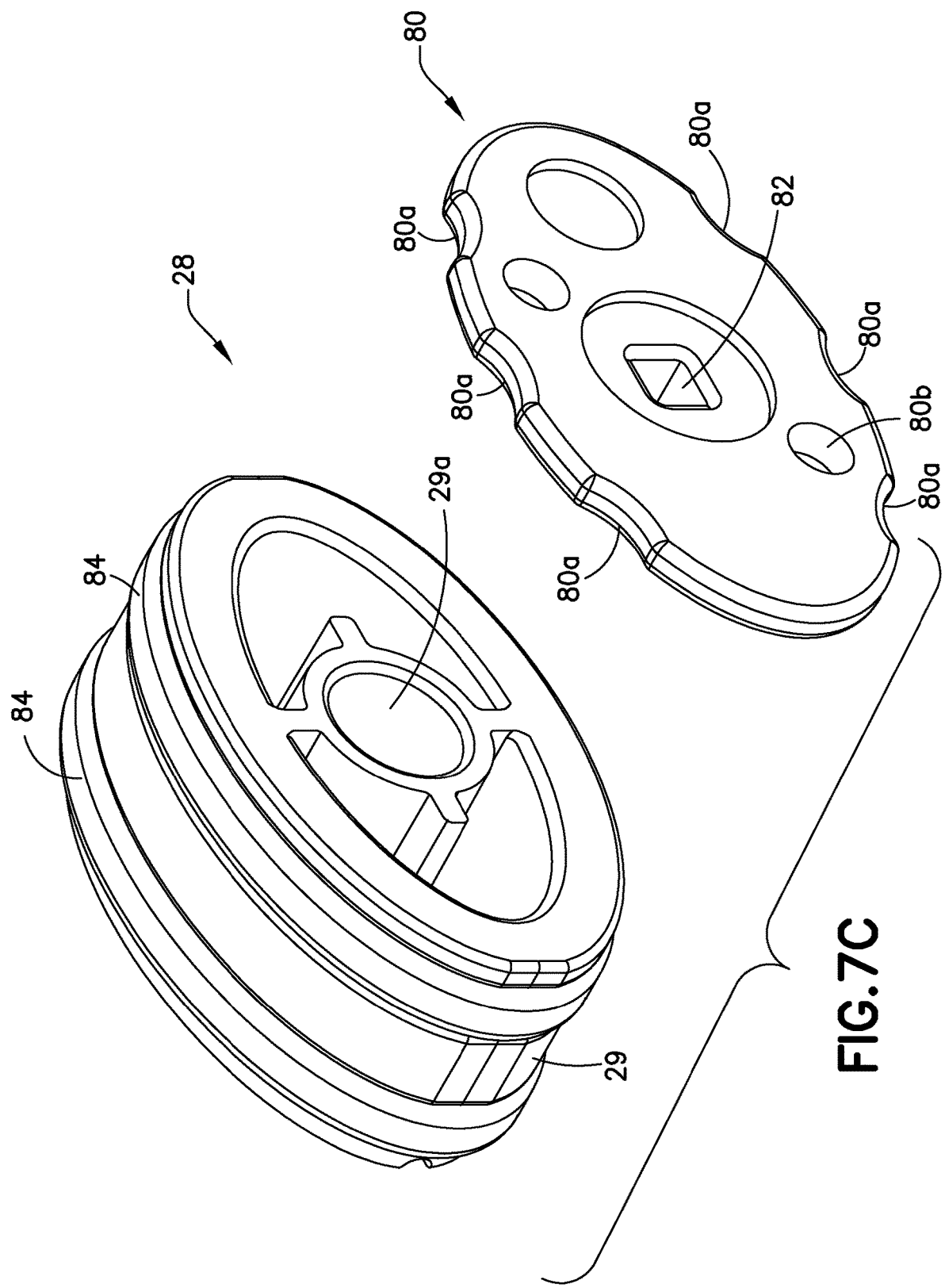

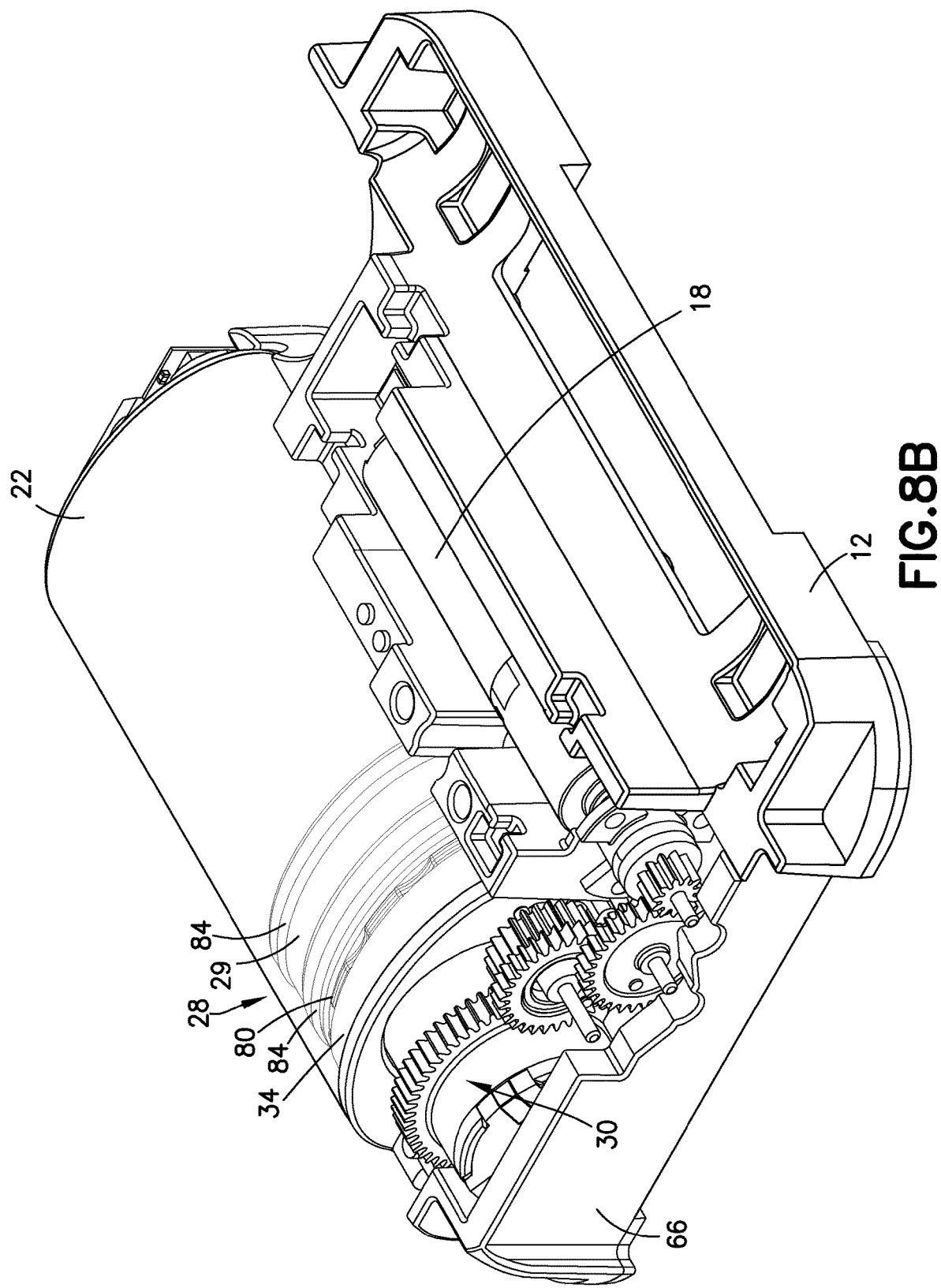

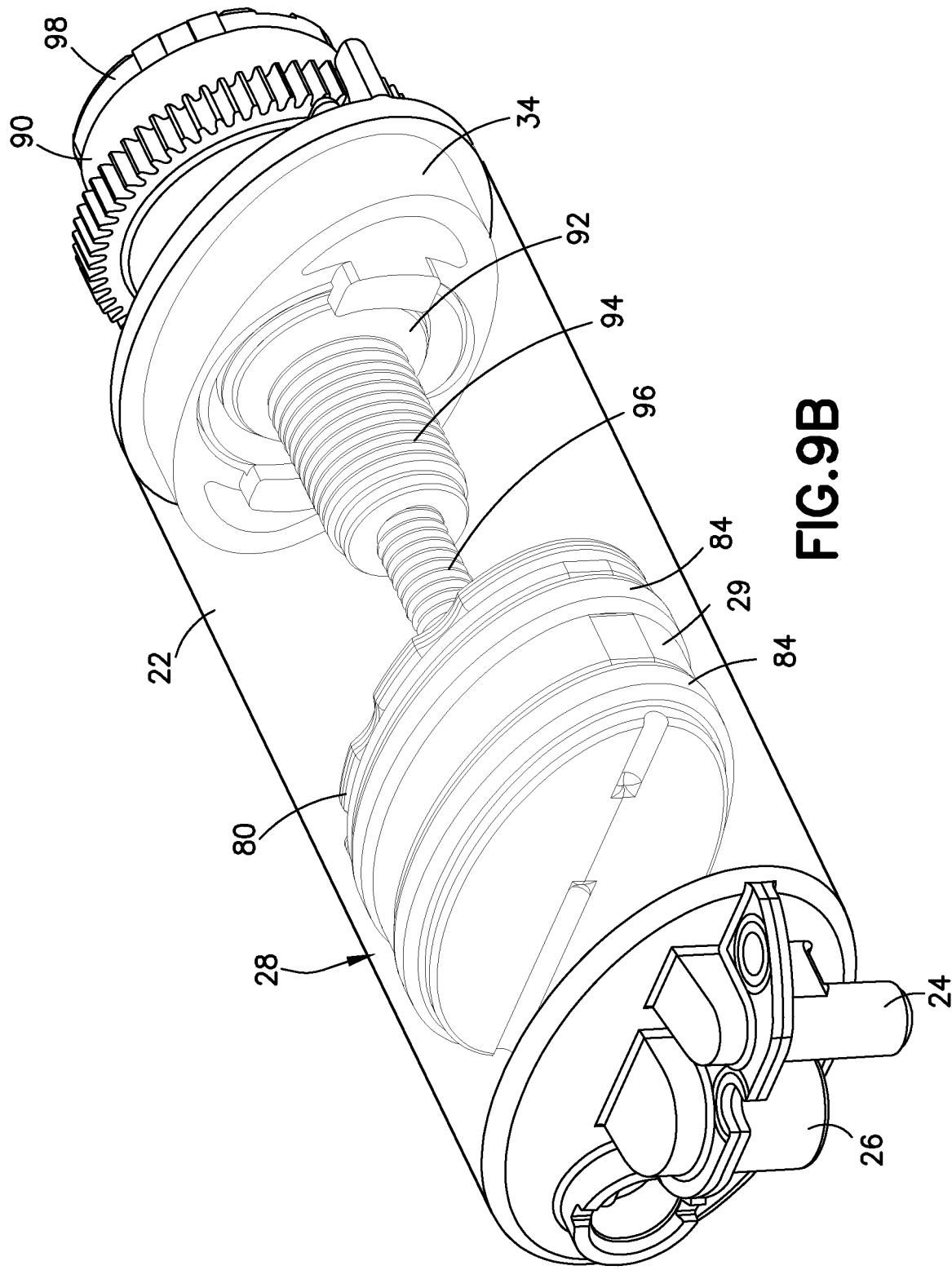

MULTIPLE TELESCOPING SCREW-DRIVEN PUMP MECHANISM WITH ANTI-ROTATION OF INNERMOST SCREW KEYED TO RESERVOIR PLUNGER IN FLUID DELIVERY DEVICE

This application claims the benefit of U.S. provisional application Ser. No. 63/066,851, filed Aug. 18, 2020, the content of which is incorporated herein by reference in its entirety.

BACKGROUND

Field

Illustrative embodiments relate generally to pump mechanisms for use in fluid delivery devices such as wearable medication infusion patches. Illustrative embodiments relate generally to nesting telescopic screws for controllably extending or retracting a plunger driver in a syringe barrel-type reservoir that do not affect reservoir volume to ensure biocompatibility, that are fully retractable outside reservoir, and are keyed to the plunger for anti-rotation control.

Description of Related Art

Typical drug delivery patch pump designs are challenged by the need achieve small size, low power consumption, accurate delivery, high reliability, and low manufacturing costs. In addition, drug delivery patch pump designs cannot impact drug quality. For example, the materials used for pump mechanism components that contact the delivered fluid cannot present biocompatibility problems.

SUMMARY

The above and other problems are overcome, and additional advantages are realized, by illustrative embodiments.

Example embodiments of the present disclosure realize several advantages such as minimizing the device size envelope or form factor, while retaining the beneficial features of highly reliable and proven systems such as medication pens and pen needles, syringes, or more expensive, non-portable pumping systems that employ a lead screw drive mechanism.

An aspect of illustrative embodiments is to provide an improved and novel nesting telescopic screw design that enables the use of syringe barrel-type drug containers or similar reservoirs, which have been proven to be drug-friendly or biocompatible with drugs and other fluids delivered via fluid delivery devices.

In accordance with illustrative embodiments, a fluid delivery device is provided that comprises a reservoir comprising an outlet port at a distal end, and plunger movable along a longitudinal axis of the reservoir. The plunger is configured to provide a seal with respect to inner walls of the reservoir to prevent fluid provided in a fluid chamber defined on a first side of the plunger and comprising the outlet port from leaking into a portion of the reservoir defined by a second side of the plunger. The fluid delivery device has a plunger driver assembly mounted at a proximal end of the reservoir that comprises a plurality of nested, telescoping screws that, when an outermost drive screw is rotated, move from a nested configuration that does not extend into the reservoir to an extended configuration that extends from the proximal end of the reservoir into the reservoir. The plurality of nested, telescopic screws comprises an innermost screw that is connected to the plunger and constrained from rotation by an anti-rotation mechanism.

In accordance with aspects of the illustrative embodiments, the reservoir is a syringe barrel-type container.

In accordance with aspects of the illustrative embodiments, the anti-rotation mechanism is the reservoir and plunger having anon-circular cross-section to prevent rotation of the plunger within the reservoir when the outermost drive screw is rotated. For example, the reservoir and plunger each have an elliptical cross-section.

In accordance with aspects of the illustrative embodiments, the anti-rotation mechanism comprises a pusher disposed between the plunger and a distal end of the innermost screw. The pusher abuts a proximal side of the plunger and is configured to move along the longitudinal axis of the reservoir in response to rotation of the outmost screw.

In accordance with aspects of the illustrative embodiments, the pusher comprises a keying feature that cooperates with a corresponding keying feature on the distal end of the innermost screw to engage the innermost screw with the pusher. For example, the keying feature of the pusher comprises a detent, and the corresponding keying feature on the distal end of the innermost screw is dimensioned and/or shaped to be pressure fit into the correspondingly dimensioned and/or shaped detent. Further, the detent can comprise a through hole to a distal side of the pusher, and the distal end of the innermost screw can extend through the through hole, for example. The distal end of the innermost screw can be heat staked at the distal side of the pusher at the through hole. The through hole can comprise anti-rotation slots to facilitate heat staking. Alternatively, the pusher can comprise a protrusion on its distal side and the through hole can extend through the protrusion. In accordance with another aspect, the pusher can comprise at least one through hole for venting, and/or indents along at least a portion of its perimeter for venting.

In accordance with aspects of the illustrative embodiments, the anti-rotation mechanism comprises a detent on the second side of the plunger dimensioned to cooperate with a distal end of the innermost screw to prevent the plunger from rotating relative to the inner walls of the reservoir when the outermost drive screw is rotated. For example, the distal end of the innermost screw is dimensioned and/or shaped to be pressure fit into a correspondingly dimensioned and/or shaped detent.

In accordance with aspects of the illustrative embodiments, the plurality of nested, telescoping screws comprises the outermost drive screw having an inner diameter and inner threads dimensioned to receive a sleeve screw having external threads configured to cooperate with the inner threads to advance the sleeve screw within the outermost drive screw when the outermost drive screw is rotated.

In accordance with aspects of the illustrative embodiments, the sleeve screw has an inner diameter and inner threads dimensioned to receive the innermost screw. The innermost screw has external threads configured to cooperate with the inner threads of the sleeve screw to advance the innermost screw within the sleeve screw when the sleeve screw is rotated.

In accordance with aspects of the illustrative embodiments, a torque ratio of the innermost screw is less that a torque ratio of the sleeve screw, and the torque ratio of the sleeve screw is less that a torque ratio of the outermost drive screw to allow the innermost screw, when constrained in rotation, to extend along the sleeve screw into the reservoir before the sleeve screw commences rotating relative to the outermost drive screw and advancing into the reservoir.

In accordance with aspects of the illustrative embodiments, the plurality of nested, telescoping screws have right handed threads, and respective inner screw parameters and outer screw parameters that employ the same pitch. Alternatively, the plurality of nested, telescoping screws have left handed threads, and respective inner screw parameters and outer screw parameters that employ the same pitch.

In accordance with aspects of the illustrative embodiments, the reservoir further comprises a gear anchor mounted to its proximal end, the gear anchor comprising an aperture dimensioned to receive a distal end of the outermost drive screw and allow the nested, telescoping screws to extend into the reservoir when the outermost drive screw is rotated. For example, the gear anchor is disc-shaped and dimensioned to be press fit into the proximal end of the reservoir. For example, the aperture in the gear anchor can be configured to provide stable support for the outermost drive screw while allowing the outermost drive screw to be rotated relative to the gear anchor. In addition, the gear anchor can have a through hole for venting.

In accordance with aspects of the illustrative embodiments, when the plunger driver assembly is in its nested configuration, the distal end of the innermost screw is flush with respect to a distal side of the gear anchor.

In accordance with aspects of the illustrative embodiments, when the plunger driver assembly is in its nested configuration, the distal end of the innermost screw protrudes from a distal side of the gear anchor a designated length corresponding to a depth of a detent provided on either of the second side of the plunger or an intermediate pusher between the plunger and the distal end of the innermost screw.

In accordance with aspects of the illustrative embodiments, the fluid delivery device comprises a thrust bearing feature provided relative to the plunger driver assembly and a support structure of the plunger driver assembly to minimize axial thrust load from the telescoping screw. For example, the thrust bearing feature can comprise a cap disposed on the outermost drive screw, the cap having a boss for contacting a portion of the support structure to resist an axial thrust load directed toward the proximal end of the plunger driver assembly and generated by the plunger driver assembly, plunger or fluid in the fluid chamber.

Additional and/or other aspects and advantages of illustrative embodiments will be set forth in the description that follows, or will be apparent from the description, or may be learned by practice of the illustrative embodiments. The illustrative embodiments may comprise apparatuses and methods for operating same having one or more of the above aspects, and/or one or more of the features and combinations thereof. The illustrative embodiments may comprise one or more of the features and/or combinations of the above aspects as recited, for example, in the attached claims.

BRIEF DESCRIPTION OF THE DRAWINGS

The above and/or other aspects and advantages of embodiments of the illustrative embodiments will be more readily appreciated from the following detailed description, taken in conjunction with the accompanying drawings, of which:

FIGS. 7A, 7B and 7C depict, respectively, a plunger stopper and pusher assembly configured to be keyed to an innermost nested screw in accordance with example embodiments;

FIGS. 8A and 8B are a top view and a top perspective view, respectively, of a fluid delivery device with its cover removed for clarity to depict a plunger driver assembly constructed in accordance with another example embodiment that employs a four-layer telescopic lead screw design;

FIGS. 9A, 9B and 9C illustrate respective positions of the plunger drive assembly of FIGS. 8A and 8B;

Throughout the drawing figures, like reference numbers will be understood to refer to like elements, features and structures.

DETAILED DESCRIPTION OF ILLUSTRATIVE EMBODIMENTS

Figure 1:
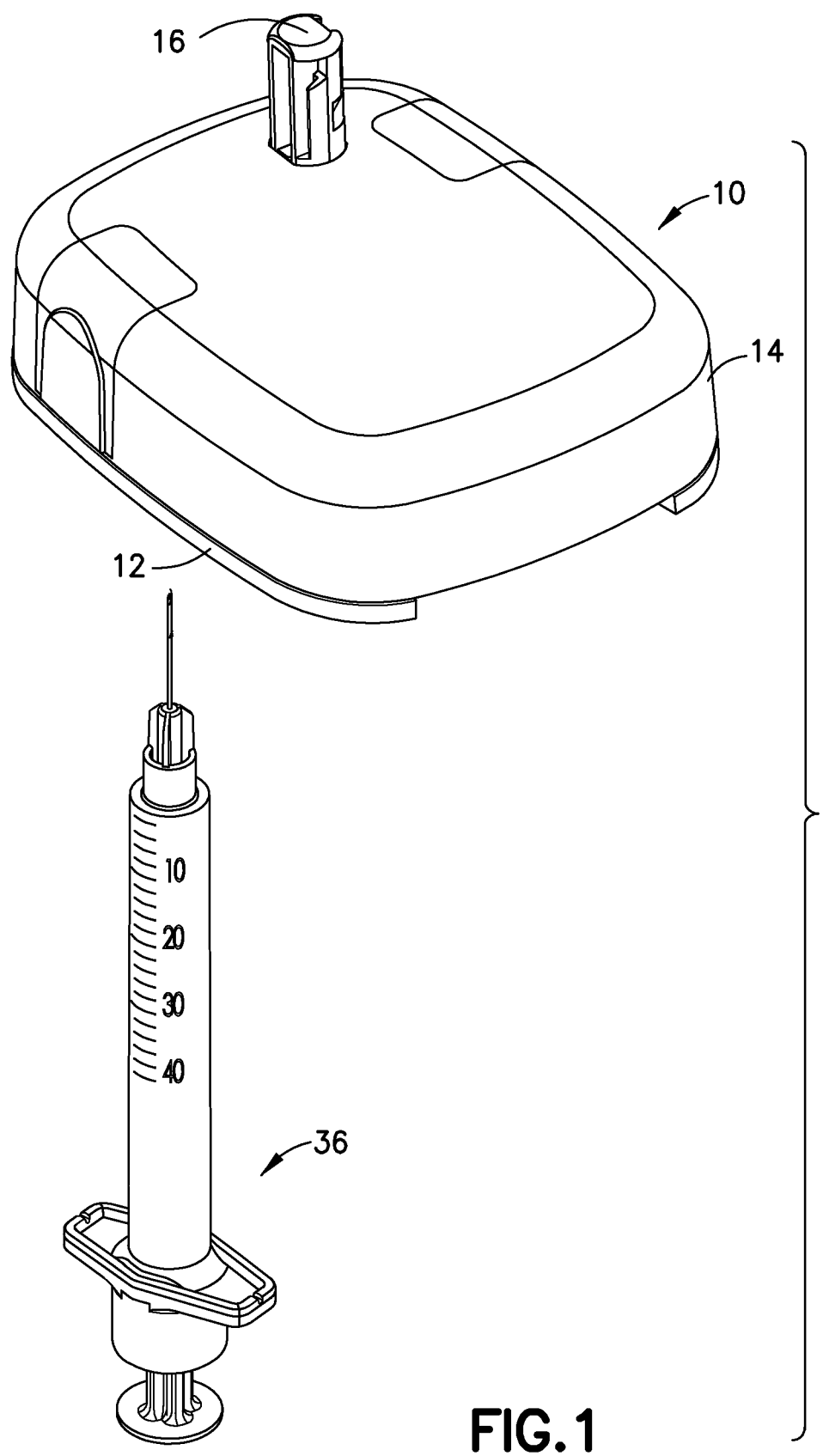
FIG. 1 is a perspective view of a wearable fluid delivery device constructed in accordance with an example embodiment.

As will be appreciated by one skilled in the art, there are numerous ways of carrying out the examples, improvements, and arrangements of a pump in accordance with embodiments disclosed herein. Although reference will be made to the illustrative embodiments depicted in the drawings and the following descriptions, the embodiments disclosed herein are not meant to be exhaustive of the various alternative designs and embodiments that are encompassed by the disclosed technical solutions, and those skilled in the art will readily appreciate that various modifications may be made, and various combinations can be made with departing from the scope of the disclosed technical solutions.

Example embodiments of the present disclosure realize several advantages such as minimizing the device size envelope or form factor, while retaining the beneficial features of highly reliable and proven systems such as medication pens and pen needles, syringes, or more expensive, non-portable pumping systems that employ a lead screw drive mechanism. In accordance with example embodiments described herein, a novel nesting telescopic screw design is employed that enables the use of syringe-based drug containers or similar reservoirs, which have been proven to be drug-friendly or biocompatible with drugs and other fluids delivered via fluid delivery devices.

FIG. 1 is a perspective view of a wearable fluid delivery device 10 constructed in accordance with an example embodiment. The drug delivery device 10 comprises a baseplate 12, a cover 14, and an insertion mechanism 16 in an undeployed position. A reservoir fluid delivery device 10 can be filled with the fluid (e.g., drug) by a user inserting a needle of a filled syringe 36 into a fill port (not shown) provided in the baseplate 12 that has an inlet fluid path from the fill port to the reservoir. It is to be understood that the fluid delivery device 10 can be filled with a fluid (e.g., drug) using different mechanisms and methods.

Figure 2:
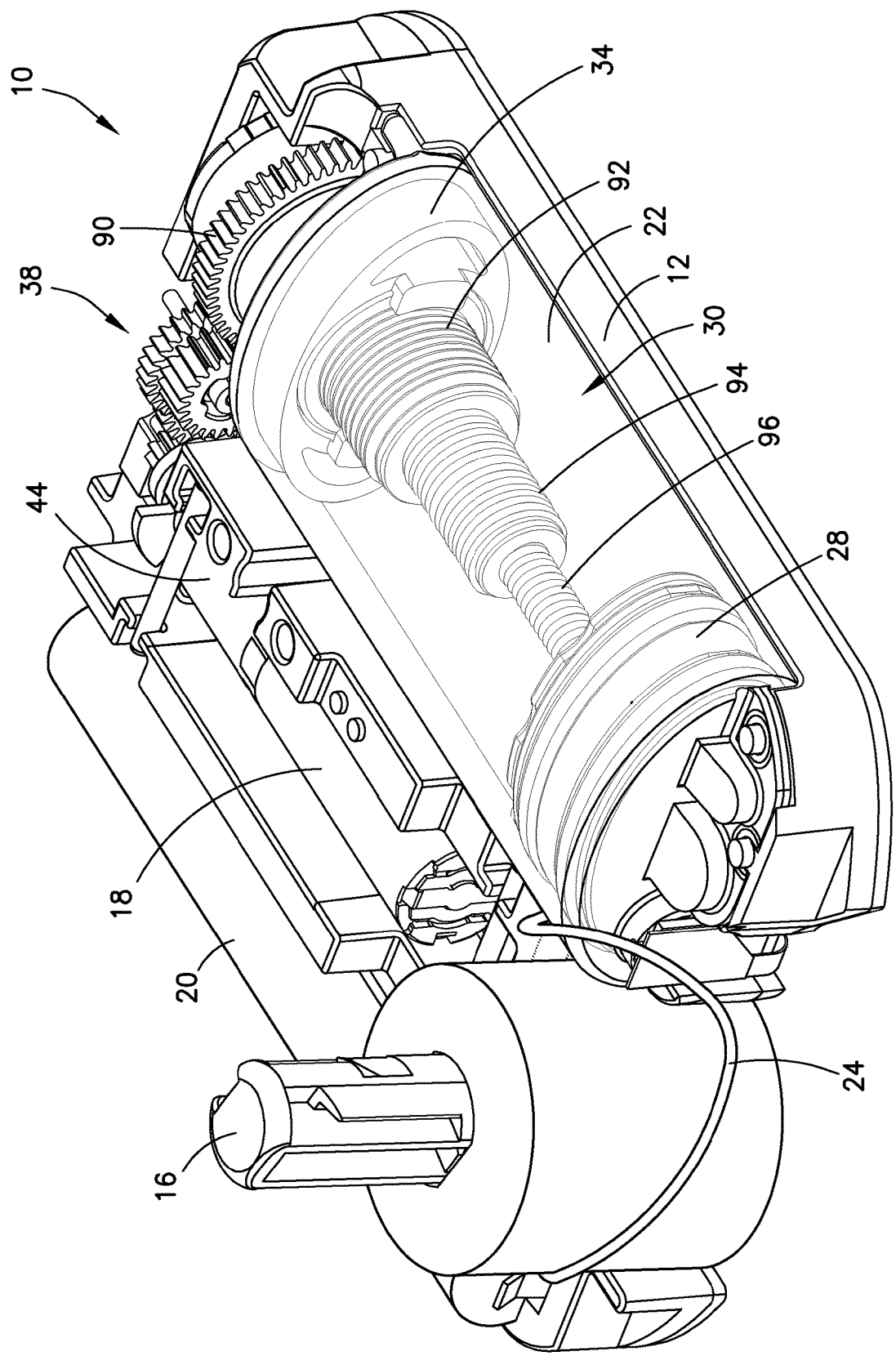
FIG. 2 is a perspective view of the fluid delivery device of FIG. 1 with the cover removed.

FIG. 2 is a perspective view of the fluid delivery device of FIG. 1 with the cover removed. The baseplate 12 supports the insertion mechanism 16, a motor 18, a power source such as a battery 20, a control board (not shown), and a reservoir 22 or container for storing a fluid to be delivered to a user via an outlet fluid path 24 from an outlet port of reservoir to the insertion mechanism 16. The reservoir 22 can also have an inlet port connected via an inlet fluid path 26 to a fill port (e.g., provided in the baseplate 12). The reservoir 22 contains a plunger 28 having a stopper assembly 29. The proximal end of the reservoir 22 is also provided with a plunger driver assembly 30 having plural telescopic nested screws, a gear anchor 34, an outermost drive screw 36 that is rotated via a gear train 38 connected to the motor 18. Although a gear train 38 is shown for illustrative purposes, the drive mechanism can be gears, ratchets, or other methods of inducing rotation from a motor.

Figure 3:
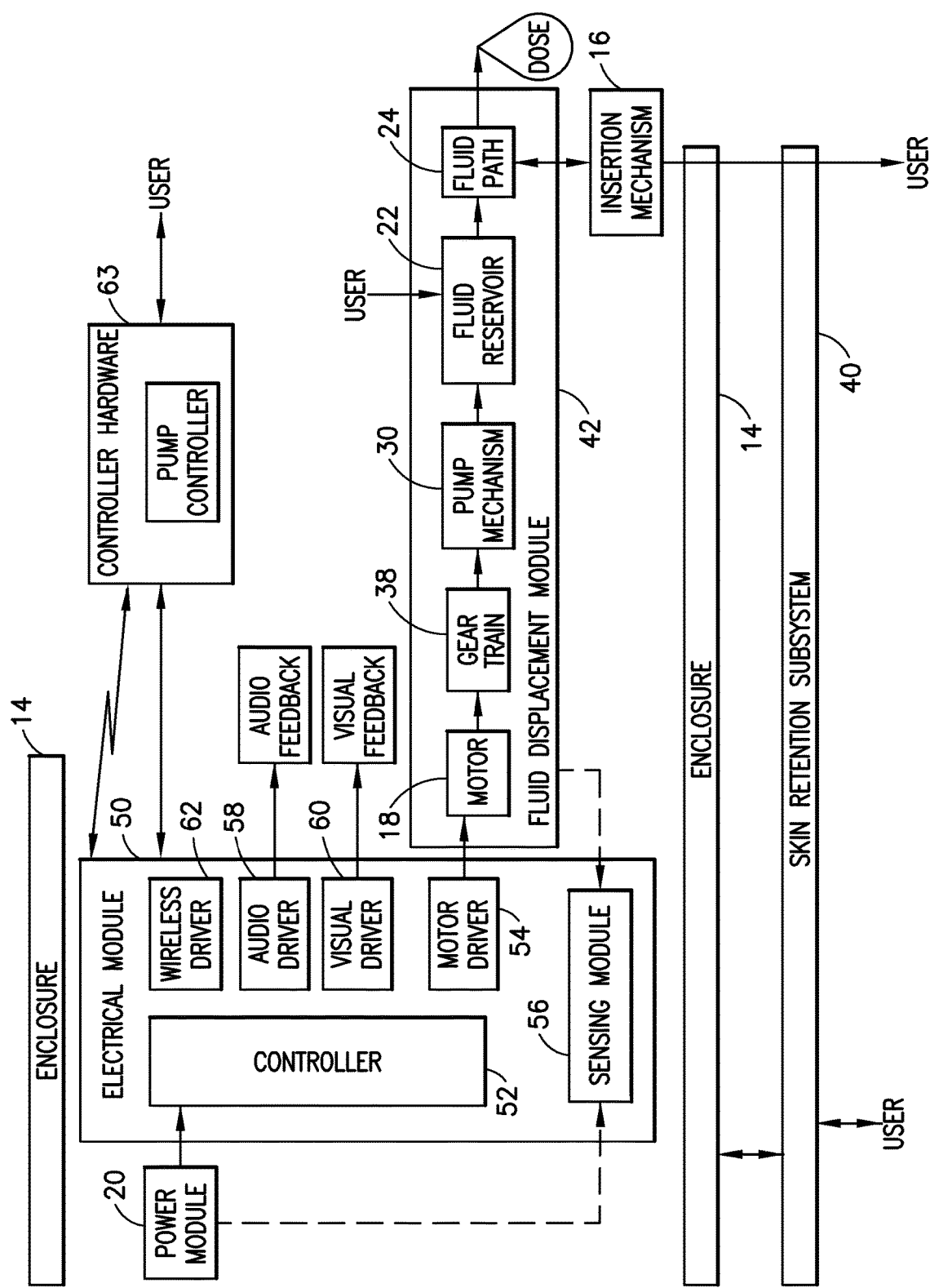
FIG. 3 is a block diagram of example components of a fluid delivery device constructed in accordance with an example embodiment.

FIG. 3 is a block diagram of example components of a fluid delivery device constructed in accordance with an example embodiment. The cover/housing or device 10 housing is indicated at 14. The device 10 has skin retention subsystem 40 such as an adhesive pad to connect the device 10 to a user's skin. The fluid delivery device 10 further comprises the reservoir 22, the insertion mechanism 16, and a fluid displacement module 42 that can include the motor 18, gear train 38, pump mechanism (e.g., plunger driver assembly 30), and outlet path 24. The fluid delivery device further comprises electrical components such as a power module (e.g., battery 20), and an electrical module 50 comprising a controller 52, a motor driver 54, optional sensing module 56 to sense fluid flow conditions (e.g. occlusion or pump mechanism runaway), optional audio driver 58 (e.g., to indicate dosing in progress, low reservoir, occlusion, successful pairing with external device, or other condition via an audible alarm such as a buzzer), and an optional visual driver 60 to provide visual feedback via a light emitting diode(s) and/or optional tactile driver to provide tactile feedback via a vibration component, and an optional wireless driver 62 for wireless communication between the fluid delivery device and an optional remote pump control device (e.g., a smartphone or dedicated controller 63). With regard to the sensing module 56, the fluid delivery device can be provided, for example, with one or more encoders to provide feedback of the drive mechanism (e.g., plunger driver assembly 30) for indexing and pump mechanism runaway prevention purposes.

Figure 4A:
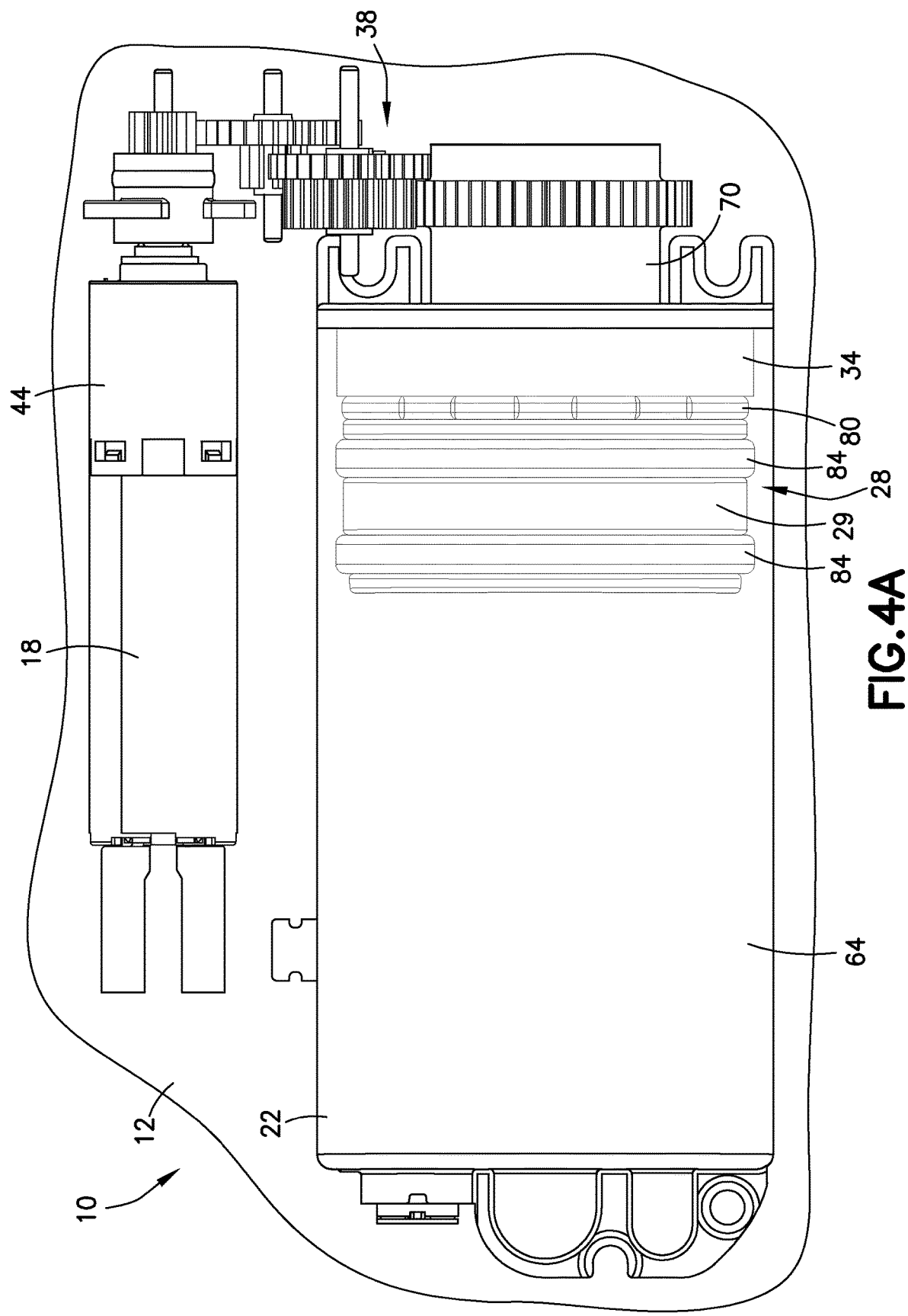
FIGS. 4A and 4B are a top view and a top perspective view, respectively, of a fluid delivery device with its cover removed for clarity to depict a plunger driver assembly constructed in accordance with an example embodiment.
Figure 4B:
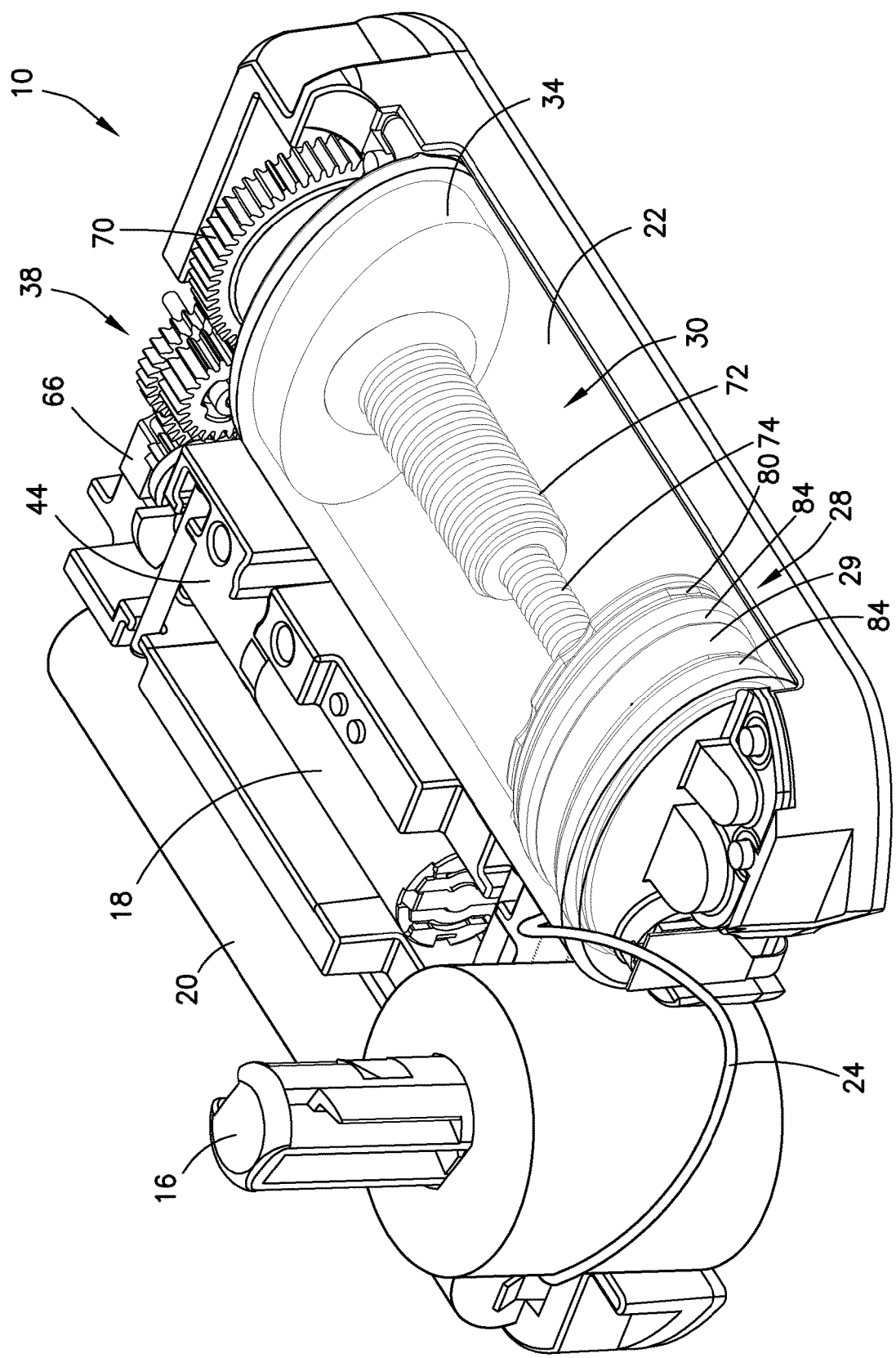

FIGS. 4A and 4B are a top view and a top perspective view, respectively, of a fluid delivery device with its cover removed for clarity to depict a plunger driver assembly constructed in accordance with an example embodiment. The plunger driver assembly 30 is shown fully retracted in FIG. 4A and fully extended in FIG. 4B. It is to be understood that the motor 18 can control the plunger driver assembly 30 to move the telescoping screw members incrementally from the fully retracted to the fully extended positions shown to deliver respective designated dose amounts of fluid from a fluid chamber portion 64 of the reservoir 22. The motor 18 and gear train 38 rotate an outermost drive screw 70 on the plunger driver assembly 30. The gear train 38 can have different configurations. For example, the gear train 38 can also be in the form of a ratchet indexing mechanism or other indexing mechanism that precisely rotates the drive nut or outmost drive screw 90 by a mechanically controlled amount. The motor 18 and related gear train components 38 and the outermost drive screw 70 of the plunger driver assembly 30 can be mounted with respect to each other via a mounting plate 66 or other mechanism secured to the baseplate 12. The reservoir 22 can be secured to the baseplate 12 via a reservoir mount (e.g., a wall on the baseplate 12, the mounting plate 66, a superstructure or other structure in the device housing 14). As shown in FIG. 4B, the motor housing 44 secures the motor 18 with respect to the baseplate 12 and housing and baseplate can be an integral component.

With continued reference to FIG. 4B, an inlet fluid path can be provided from a fill port (not shown) on the underside of baseplate 12 to an inlet port (not shown) of the reservoir 22 to allow filling of the reservoir prior to shipment, or by a user prior to using the fluid delivery device 10. A gear anchor 34 is provided at a proximal end of the reservoir 22, and is stationary with respect to the reservoir 22. The plunger 28 is provided within the reservoir 22 and configured to be controllably translated along a longitudinal axis of the reservoir 22 by the plunger driver assembly 30 and motor 18 operation.

Figure 5:
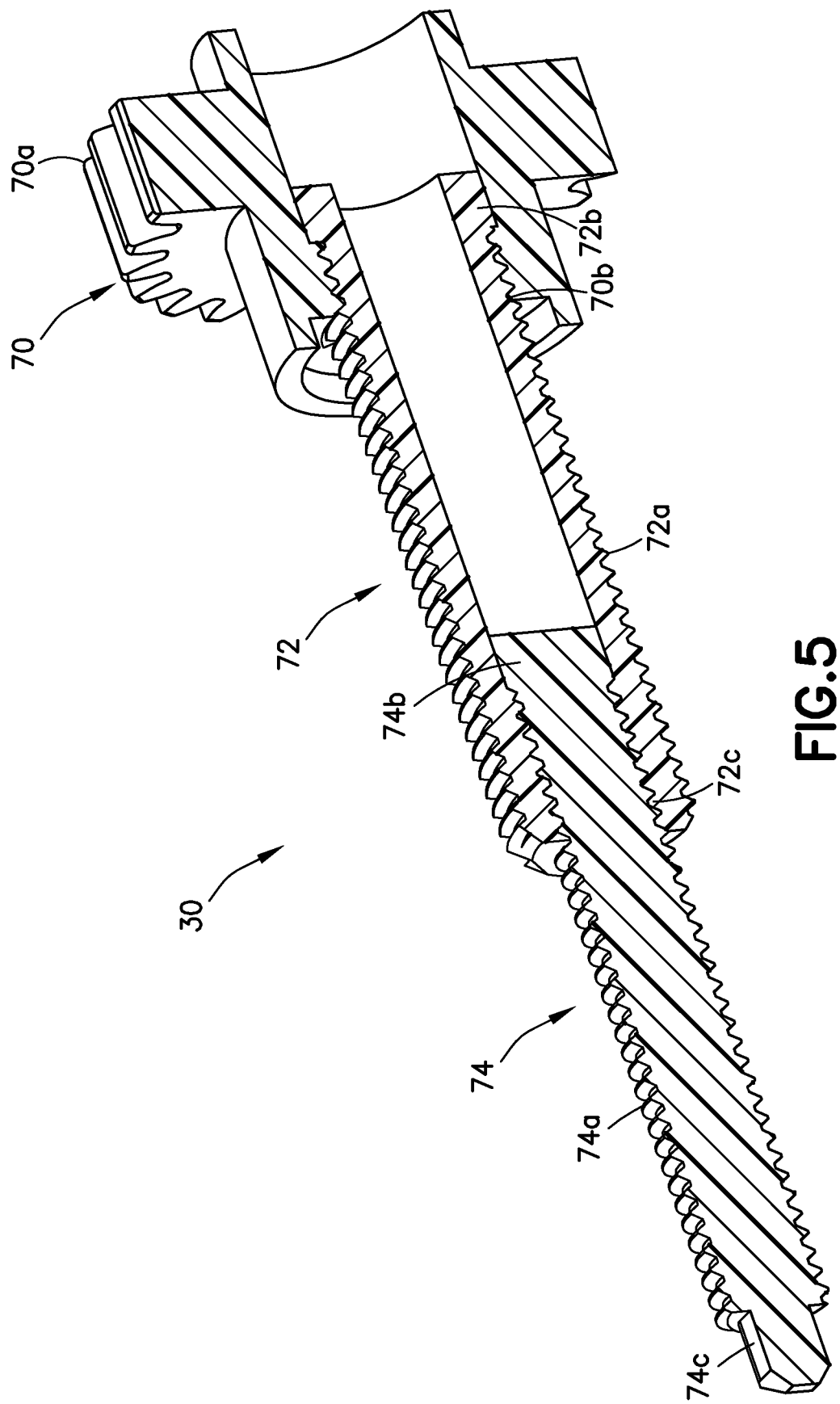
FIG. 5 depicts a plunger drive assembly constructed in accordance with an example embodiment and comprising a three-layer telescopic lead screw design.

FIG. 5 shows a plunger driver assembly 30 in accordance with an example embodiment comprising a three-layer telescopic lead screw comprising an outermost drive screw 70, a sleeve screw 72 and an innermost screw 74. The outermost drive screw 70 has a first portion with drive gear teeth 70a that cooperate with teeth on an adjacent gear of the gear train 38 actuated by motor 18, and threaded aperture 70b that cooperates with outer threads 72a of a sleeve screw 72. The sleeve screw 72 has an end feature 72b at the proximal end thereof to prevent the sleeve screw 72 from being driven from outermost drive screw 70, and a threaded aperture 72c at the distal end thereof with internal threads that cooperate with outer threads 74a of an innermost screw 74. The innermost screw 74 has an end feature 74b at a proximal end thereof to prevent the innermost screw 74 from being driven from the sleeve screw 72, and a keying feature 74c at the distal end thereof. The keying feature 74c can be a selected shape or protrusion or other feature or component that couples the innermost screw 74 to a cooperating keying feature on the plunger 28 while constraining the innermost screw 74 from rotating with respect to the plunger 28 when the outermost screw 70 is rotated by the motor 18 and gear train 38. In other words, when the outermost drive screw 70 is driven via the motor 18 and the gear train 38, the distal end of the innermost screw 74 is anchored inside the plunger 28 or other surface of the plunger driver assembly 30. The outermost drive screw 70 rotates clockwise advancing the sleeve screw 72 and the innermost screw 74. The screw members 70, 72 and 74 have right handed threads, for example, but could also be designed to all have left handed threads. For example, each of the screw members 70, 72 and 74 has the same inner and/or outer screw designs with same pitch and slight variations on the other parameters.

In accordance with an example embodiment, drive screw 70's length is dimensioned such that, when the screws are all nested or collapsed, they are all contained in the drive screw 70. In addition, the drive screw 70 is provided with a thrust bearing cap 98 at the proximal end thereof to help the device 10 absorb axial thrust loads, as described further below.

In accordance with another example embodiment, a pusher 80 is provided as a separate component between the inner screw 74 and the plunger 28. The pusher 80 can be provided with a keying feature (e.g., 82) instead of the plunger 28 to receive the keying protrusion or other feature 74c from the innermost screw 74, and is overall shaped to prevent rotation of the innermost screw 74. An advantage of using a pusher 80 is that its design can be made to reduce off-axis forces that could negatively affect the precision of the motion and overall volume delivery due to uncontrolled plunger wobble.

The torque ratios between screws 72 and 74 are related to each component's diameter, with the smallest drive torque associated with the smaller diameter of the innermost screw 74. Under optimal conditions, the innermost or smallest screw 74 likely drives forward first, when constrained in rotation by the plunger 28 surface or other surface or member to which it is anchored. Next, the sleeve screw 72 starts rotating and advancing. Manufacturing variation and tolerances can cause changes in advance movement sequencing, however, parts generally only advance according to the common pitch of each part. Except for the outermost drive screw 70 with the drive gear teeth 70a, each inner screw will require an end feature that prevents the screw from being driven out of the assembly package. In order to minimize size, this feature length can be minimized. This feature, however, will also help to stabilize the axial motion of the screw and prevent motion that is not axially oriented.

The innermost screw 74 requires a keying feature to engage the plunger 28. This keying feature can either engage with a non-circular plunger geometry, whereby rotation is prevented by geometry, or can be engaged with an intermediate structure (e.g., a pusher 80) that acts to prevent rotation in the operating syringe barrel. This end feature 74c is optimally smaller than the outer thread of the same innermost screw 74 so that it may be assembled from the rear end of the assembly 30. For example, the distal end of the innermost screw 74 can be dimensioned and/or shaped to engage a corresponding dimensioned and/or shaped detent or indent 82 in the plunger 28 or pusher 80 that prevents any rotation imparted on the innermost screw 74 by the other components 70 and 72 from causing rotation of the plunger 28 relative to the inner walls of the reservoir 22. The keying feature 74c on the distal end of the innermost screw is smaller than the threads and have features and/or shape so that it presses or engages solidly into the pusher to avoid relative rotation. If necessary, other, stronger, larger features can be attached to the front or distal end of the screw 74. This design can employ an elliptical syringe barrel-type reservoir 22 to contain the drug and provide anti-rotation functionality. The elliptical shape also has the added benefit of potentially saving device height. In addition, the telescopic nested lead screw design of the example embodiments can be complemented by a suitable ratcheting/indexing mechanism to further improve the delivery resolution.

Figure 6A:
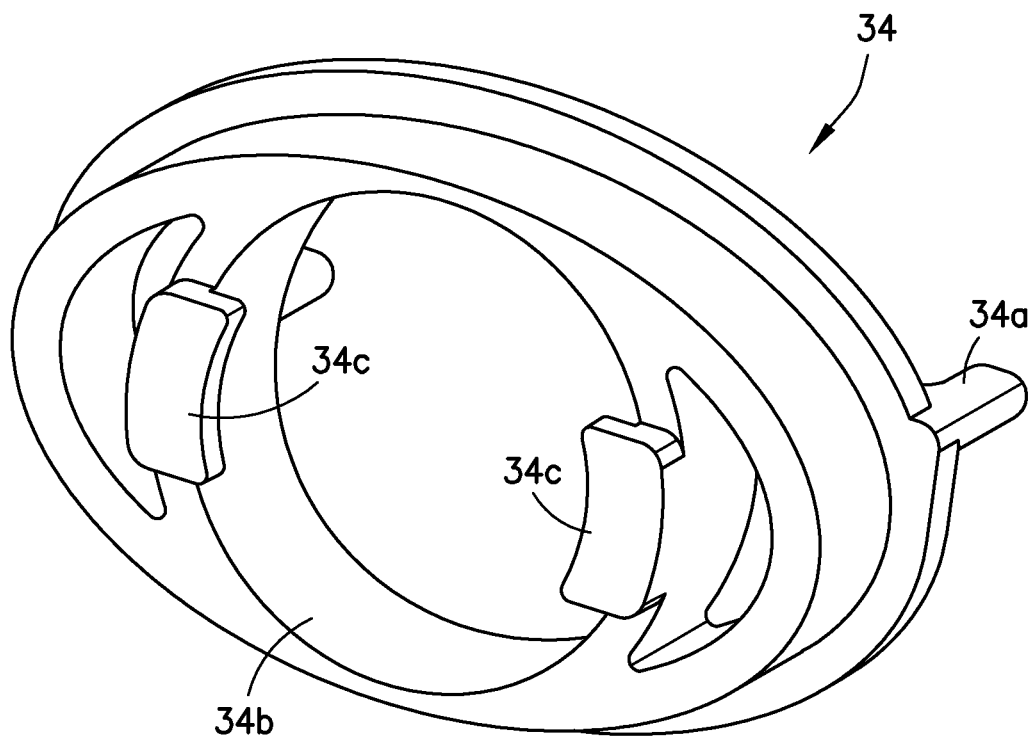
FIGS. 6A and 6B depict, respectively, a rear perspective view and a front perspective view of a gear anchor in accordance with an example embodiment.
Figure 6B:
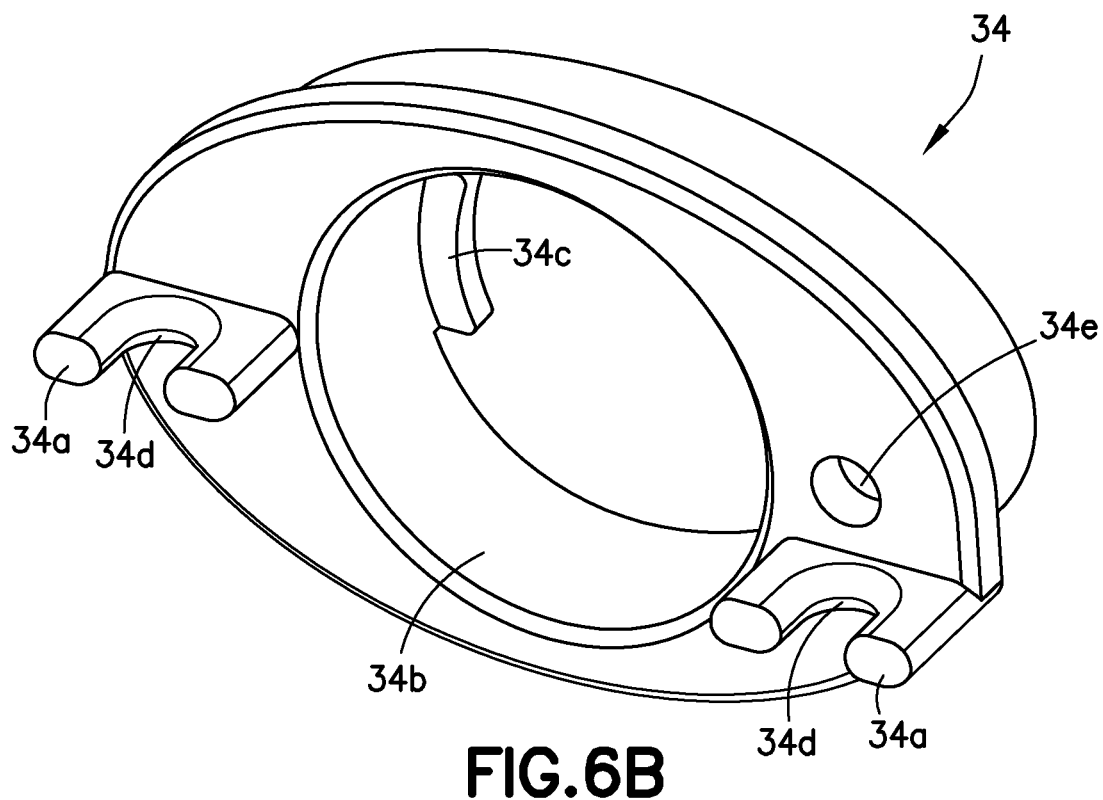

FIGS. 6A and 6B depict, respectively, a rear perspective view and a front perspective view of the gear anchor 34 in accordance with an example embodiment. The gear anchor 34 is a disc-shaped member inserted into an opening at the proximal end of the reservoir 22 and can have optional features such as protrusion(s) 34a with slot 34d to facilitate a press or snap fit with respect to pins 66a on a reservoir mount. The gear anchor 34 has an aperture 34b dimensioned to receive the distal end 70d of the outermost drive screw 70 having smaller circumference than first portion 70a and a lip 34c that cooperates with distal end of the outermost drive screw 70 to secure the outermost drive screw 70 against gear anchor 34. It is to be understood that the lip or flange 34c can be removed to reduce axial footprint of the screw-train. Its function is limited as typical loads are reacted in a direction opposing the face. In an alternative arrangement, a ring can be added to the drive screw 70 that would bear on the outer surface of the reservoir cap or gear anchor 34. The gear anchor 34 also has at least one aperture or through hole 34a for venting. As described below, the pusher 80 can also have an opening(s) and/or clearances to allow venting as it moves axially in the reservoir 22.

Figure 7A:
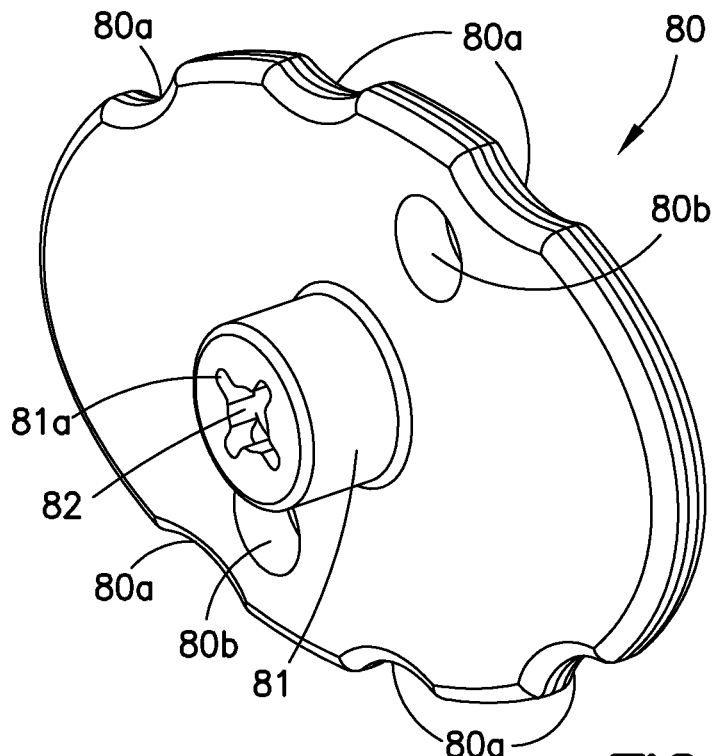
Figure 7B:
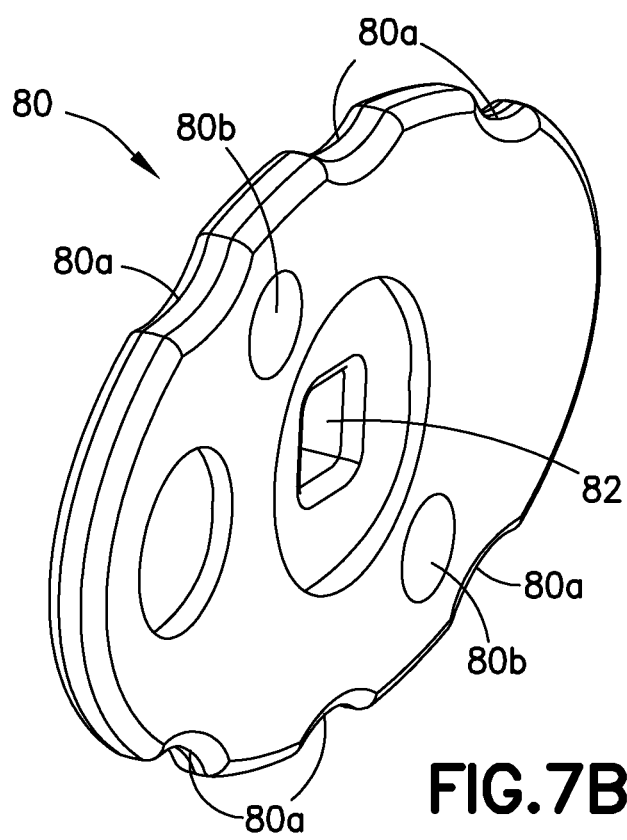

FIGS. 7A, 7B and 7C depict, respectively, a plunger 28 and stopper assembly 29 with a pusher 80 keyed to the innermost screw 74 in accordance with example embodiments. It is to be understood that the plunger 28 or an intermediate pusher 80 can comprise a disc-shaped member having a detent, indent or other feature 82 that cooperates with a keying feature 74c at the distal end of the innermost screw 74 to prevent rotation of plunger 28 relative to the reservoir 22's inner walls when the outermost drive screw 70 is being rotated within the aperture 22b by the motor 18 and gear train 34 and, as a result, screw members 72 and 74 are being extended or retracted translationally via the cooperation of their respective threads. It is to be understood that the plunger 28 can be decoupled from the screws and the intermediate member (e.g., a pusher 80) provides an anti-rotation function (e.g., a ball joint interface is provided between the distal end of innermost screw and the proximal side of the pusher 80 to limit off-axis load transfer). An optional protrusion 81 on the front surface of the pusher 80 can impact the rear surface of plunger 28. As shown in FIG. 7A, the protrusion 81 can be provided with anti-rotation slots 81a. When assembled, the post on the distal end of the innermost screw 74,96 can extend into the detent 90, through the pusher 80 and slightly beyond its protrusion 81. The post on the distal end of the innermost screw 74,96 cooperates with the slots 81a during heat-staking of the innermost screw relative to the pusher 80. The pusher 80, together with or alternatively the cap 34 on the reservoir 22, is provided with feature(s) to allow air venting. For example, an air venting feature can be provided along at least a portion of the perimeter of the pusher 80 and be in the form of a scalloped edge comprising notches 80a. When notches 80a are provided on the perimeter of the pusher 80, these features can be arranged to minimize axial translation friction by biasing design and tolerances for edges around a few of these features 80a to be more proud of the remaining notch edges so as to make first contact with the internal reservoir barrel face to prevent rotation. The pusher 80 can also be provided with one or more through holes 80b in a plate-like portion of the pusher for venting.

The plunger 28 has a stopper assembly 29 to prevent leakage of any fluid retained in a fluid chamber portion 64 of the reservoir 22. The stopper assembly 29 can comprise, for example, an elastic member 84 comprising elastic material similar to a syringe stopper and configured as disc mounted to a surface of a plunger 28 disc or as a band of material surrounding the plunger 28 disc. Alternatively, the plunger 28 can be configured to have one or more (e.g., two) circumferential groove dimensioned to accommodate respective O-ring(s). For example, using two O-rings increases stability (e.g., even in spite of an increase in length). Depending on dose accuracy requirements, a single O-ring can be a viable option; however, for high precision, two O-rings are particularly beneficial.

The configuration of the plunger driver assembly 30 components with respect to the reservoir 22 and the plunger 28 realizes a number of advantages. For example, having a plunger driver assembly 30 mounted at a proximal end of the reservoir 22 and having a nested configuration that does not extend into the reservoir until the outermost drive screw is rotated optimizes use of the reservoir chamber for fluid delivery instead of having to accommodate pre-delivery plunger driver components. In addition, the overall length of the reservoir can be substantially the same as the length of the housing, with the addition of a small amount of headspace to accommodate the gear train 34 connection to the drive gear teeth 70a of the outermost drive screw 70. Thus, the overall footprint of the pump mechanism is minimized as well as the longitudinal axis dimension of the fluid delivery device housing. The use of the plunger 28 and plunger driver assembly 30 design also minimizes contact of the pump mechanism with the fluid being delivered to ensure biocompatibility between the fluid and the fluid delivery housing. The example embodiments described herein employ nested telescoping screws of appropriate size and thread configuration to achieve a controlled movement of a syringe-barrel-type reservoir plunger 28. Screw-thread technology is well-defined and understood, and is capable of repeatable, powerful motion. When driven with an appropriate resolution-controlled motion by the motor 18, the nested screws (e.g., 72 and 74) can provide accurate movement under virtually all environmental conditions. Further, the drive mechanism (e.g., the plunger driver assembly 30) the does not affect the basic volume of the fluid chamber 64 where the drug resides, thus having no impact on any compatibility issues.

The technical solution of the example embodiments is based on a basic screw-drive mechanism where lifting torque is a function of applied axial load (force or pressure), thread pitch, friction parameters, and diameter. In some cases, the equations may be further expanded to capture the full details of thread geometry such as flank and lead angle, and many other special parameters. Industry standard sizes for ACME threads can generally be used to adjust the balance of lifting torque, power required, efficiency, and other functional parameters such as smoothness of operation and cost. Other thread forms can also be used, such as Buttress threads, to accurately control load-transfer, and minimize dosing errors. Each screw design may affect torque; therefore, changes should be made in a manner that is congruent with the capabilities of the motor and gearbox or index drive sub-system.

The design employed by the example embodiments lends itself to be driven with gear-reduction transmissions at very small scales. The torque required to move a gear is independent of the number of gears used in the system, and is mostly affected by material and geometry choices for the threads. Small motors and low gearbox ratios can therefore be employed, thereby yielding a compact device 10. Conversely, the torque will be different on each screw, with the smaller torque being on the innermost screw and the largest torque being on the outermost screw. The efficiency of power transmission is affected by the many interfaces, which can reduce overall efficiency but which can be adjusted to an acceptable level using adjusted parameters for the equations to determine desired lifting torque. Regardless, if battery power, or any other input power, is abundantly available, this design has the potential to create highly accurate pumps for many drug therapies, unlike any type of medical drug delivery pump currently available.

Figure 8A:
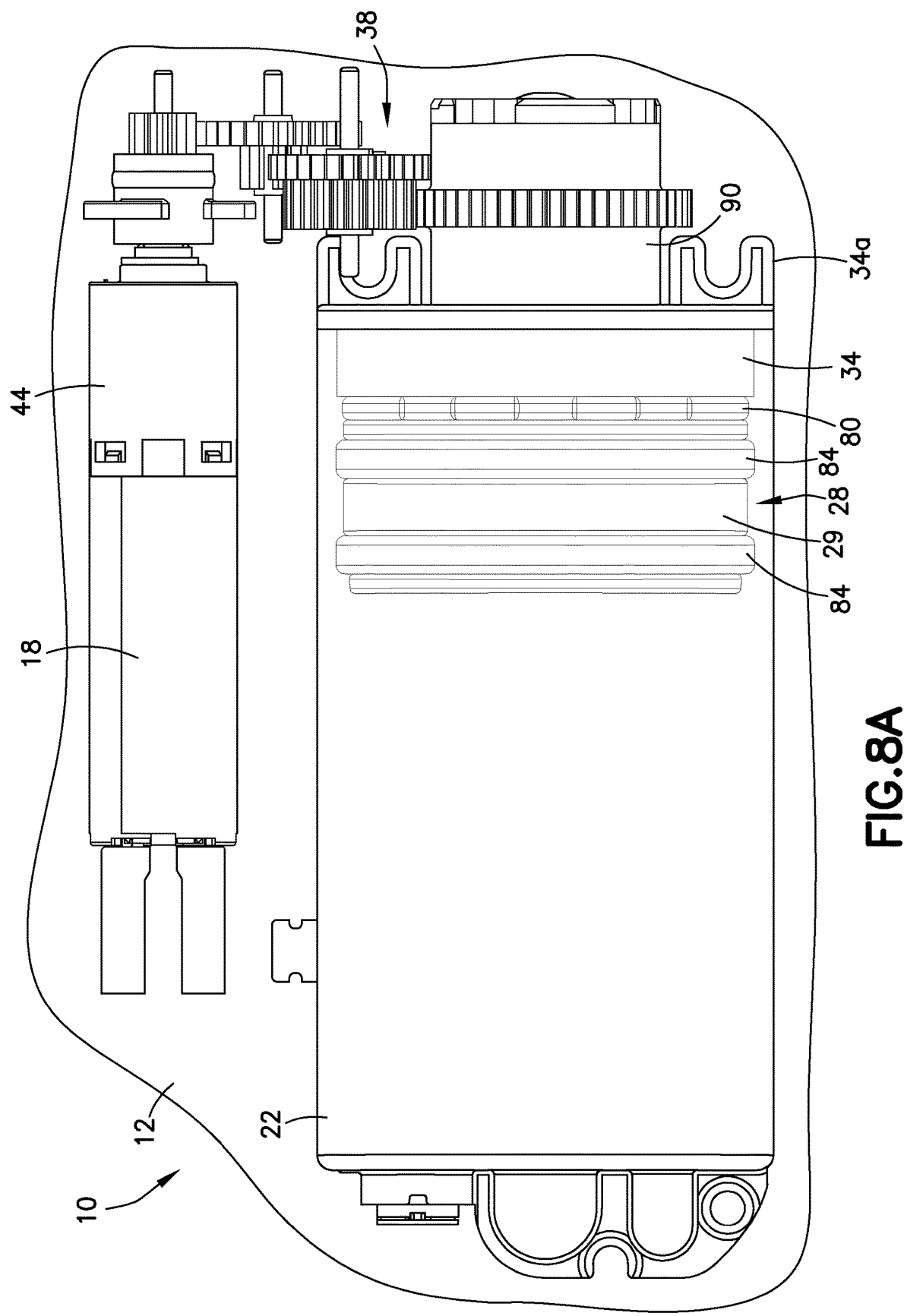
Figure 10:
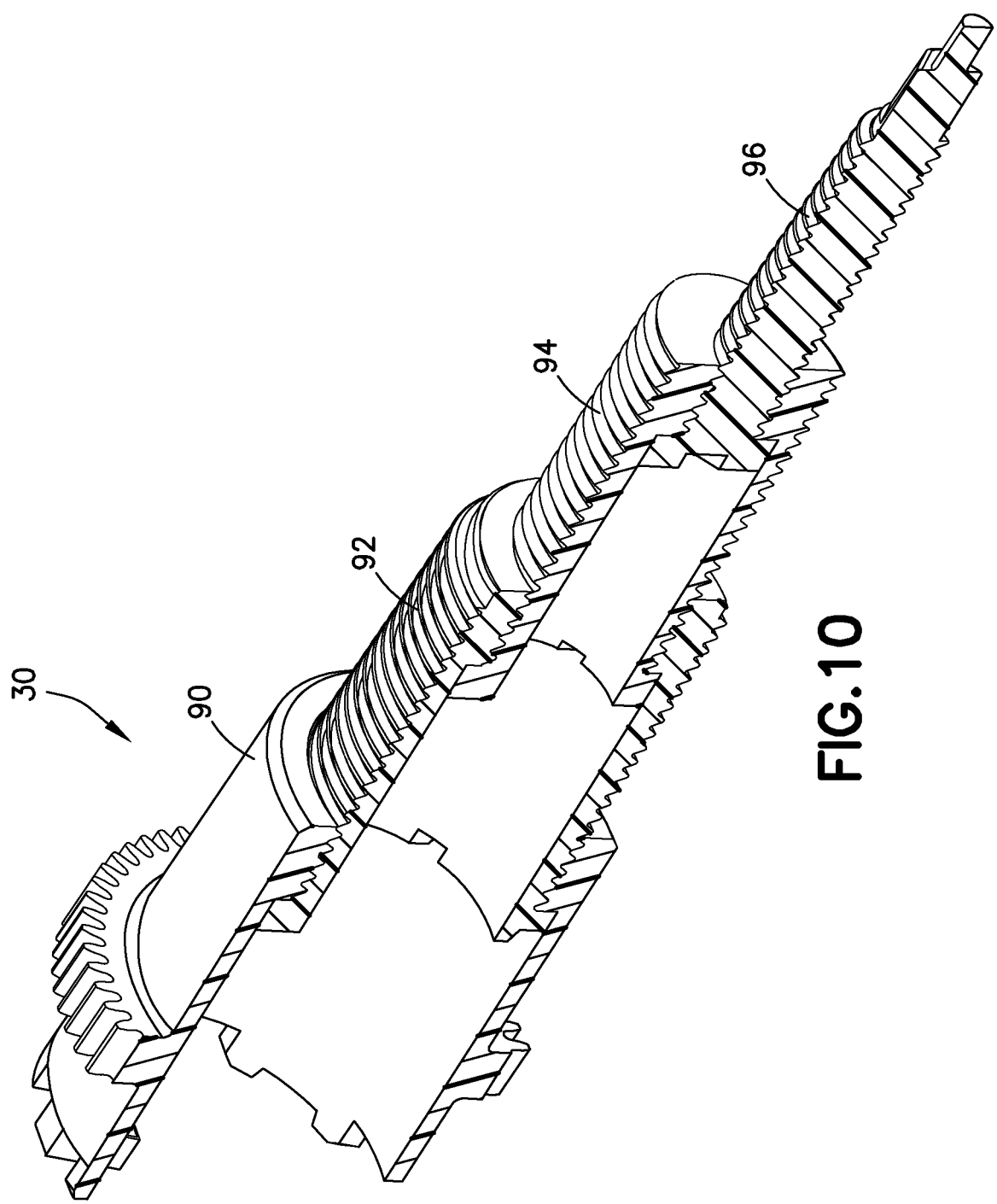
FIG. 10 depicts a plunger drive assembly constructed in accordance with an example embodiment and comprising a four-layer telescopic lead screw design.

FIGS. 8A and 8B are a top view and a top perspective view, respectively, of a fluid delivery device with its cover removed for clarity to depict a plunger driver assembly 30 constructed in accordance with another example embodiment that employs a four-layer telescopic lead screw comprising an outermost drive screw 90, a first sleeve screw 92, second sleeve screw 94 and an innermost screw 96, as illustrated in FIG. 10. Keying 82 between innermost screw 96 and the plunger 28 (or pusher 80) is similar to the above-described embodiment employing a three-layer telescopic lead screw. With reference to FIG. 10, the first sleeve screw 92, the second sleeve screw 94 and the innermost screw 96 each have an end feature at its proximal end to prevent it from being driven from the plunger driver assembly 30 in which it is nested.

Figure 9A:
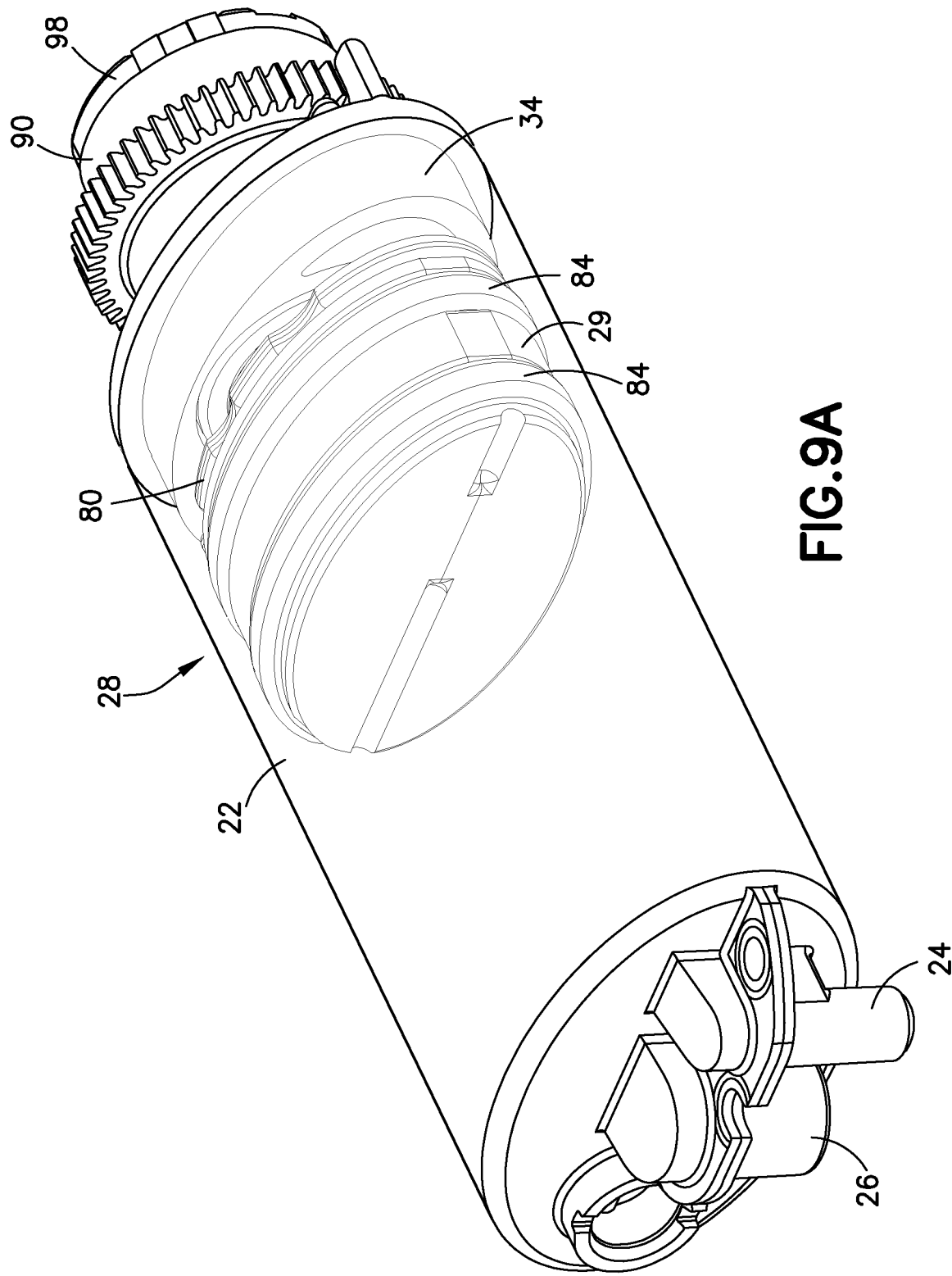
Figure 9C:
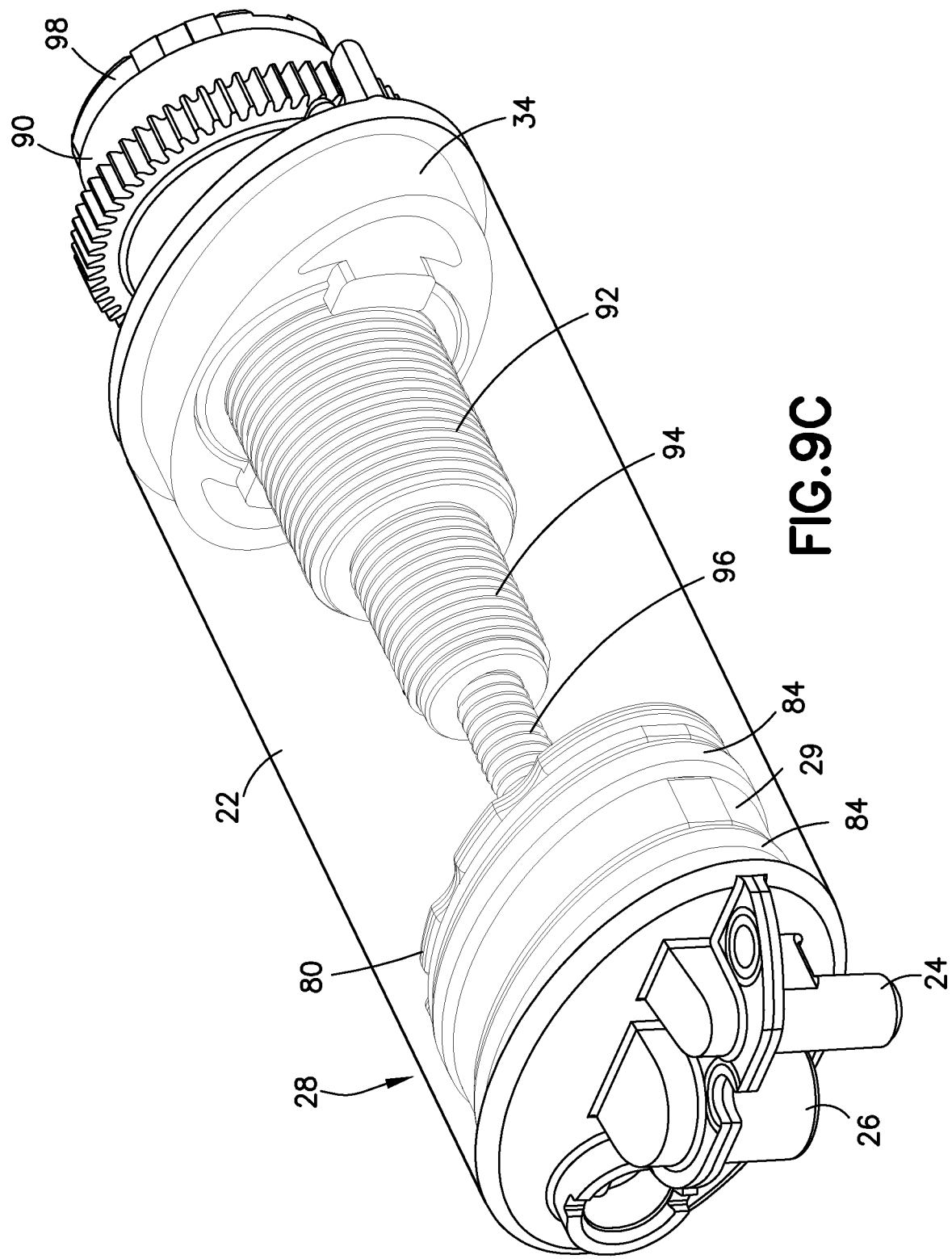
Figure 11:
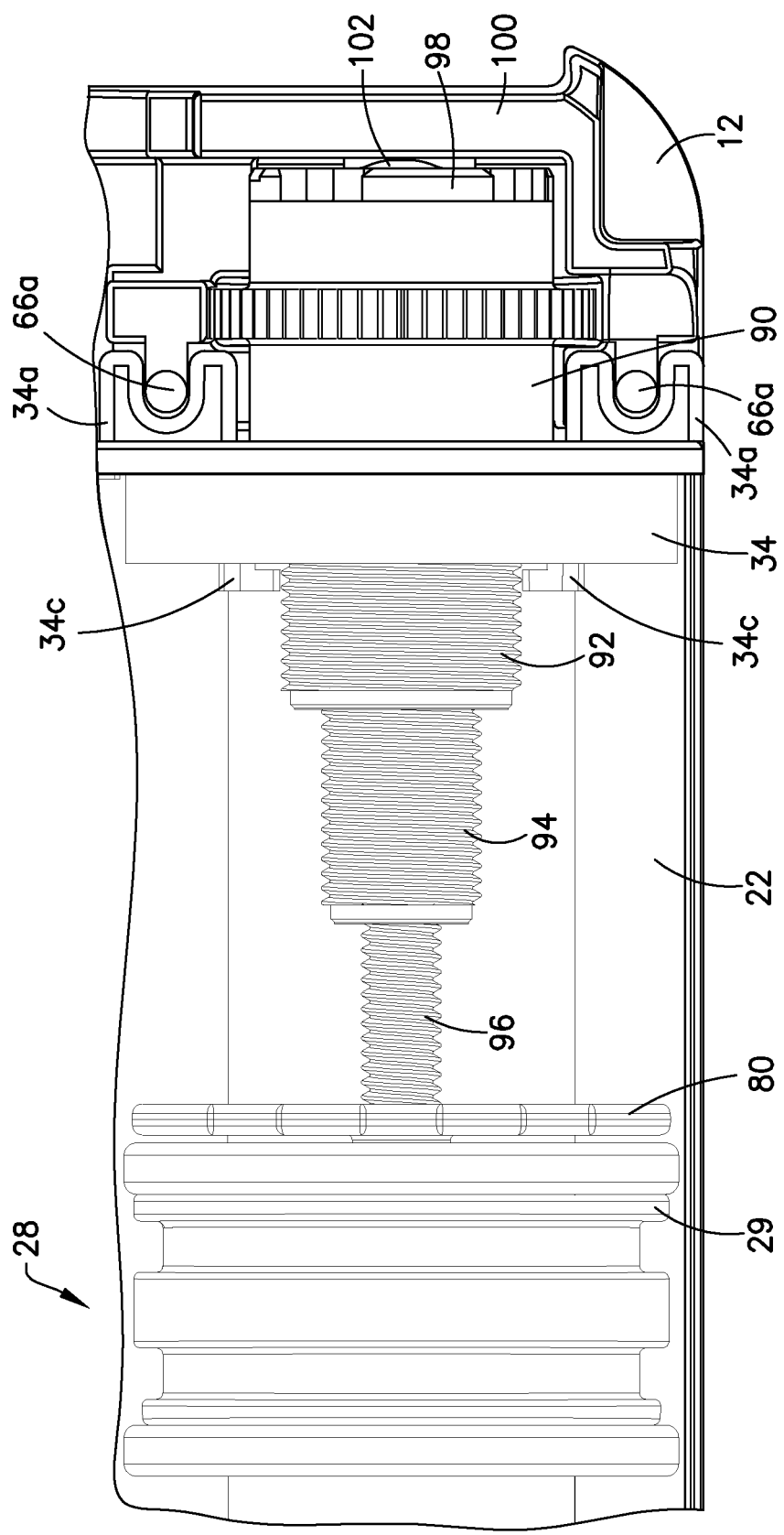
FIG. 11 is a partial side view of a fluid delivery device constructed in accordance with an example embodiment to have an axial thrust bearing feature.

The afore-mentioned thrust bearing cap 98 can be snap fit or otherwise pressed into the proximal end of the outer screw, but is shown removed in FIG. 8B and in place in FIGS. 9A-9C. As illustrated in FIG. 11 in accordance with an example embodiment, the cap 98 has a raised boss 102 that interacts with either a superstructure 66 that supports the reservoir, screws, and motor, or with a wall indicated generally at 100 on the baseplate 12. This superstructure 66 or wall 100 absorbs or minimizes axial thrust load from the screw and possibly from plunger O-rings and fluid pressure, thereby helping prevent loss of dose accuracy. The small boss 102 on the cap 98 is small in diameter so as to minimize any additional torque imposed on the drive system. The boss 102 can be dimensioned to be large enough to avoid digging and wearing into the support wall, and material choices can aid in this design. Since screw motion may cause the screw-assembly 30 to be pushed backwards, the thrust bearing cap 98 provides a benefit of handling these forces by distributing them over a small enough area to reduce torque without damaging the support structure. Alternatively, thrust can also be controlled in other locations on the drive screw or nut 70. For example, a split reservoir cap with a slot can be employed with an alternative drive nut configuration having an outer ring that rotates inside the split cap. The split cap can have press pins that allow it to be assembled around the drive nut and then inserted into the reservoir.

Both embodiments in FIGS. 4A-4B and 8A-8B, respectively, are advantageous to minimize internal reservoir 22 space used by the plunger driver assembly 30, thereby optimizing fluid chamber 64 volume while, at the same time, minimizing reservoir footprint on the baseplate and therefore overall housing dimensions. In both embodiments, the reservoir chamber 22 comprises the fluid chamber 64 and the volume taken by the plunger 28 and stopper assembly 29, and nominal reservoir volume is taken by the plunger driver assembly 30 when in its fully retracted position.

The plunger driver assembly of FIGS. 8A and 8B is shown in a fully retracted positon in FIG. 9A, an intermediate position in FIG. 9B, and a fully extended in FIG. 9C. It is to be understood that the motor 18 can control the plunger driver assembly 30 to move incrementally from the fully retracted to the fully extended positions shown to deliver a designated dose amount of fluid from the fluid chamber portion 64 of the reservoir 22. An indexer and runaway prevention device can be provided with respect to the outermost drive screw 70,90 to ensure controlled rotation of the screw 70,90 by the motor and thereby prevent runaway of the pump mechanism. For example, the drive screw or nut 70,90 can be provided with an encoder(s) for indexing and accurate dose delivery and to provide feedback to the electrical module 50 to further protect against runaway or undesirable or inaccurate pump motor action and rotation of the drive nut 70

The four-layer telescopic lead screw design in FIGS. 8A through 10 has the advantage of further travel possible within the same axial footprint as the three-layer telescopic lead screw design in FIGS. 4A through 5, at the expense of slightly larger diameter/transverse dimension. The embodiments described herein can be adapted to work from two nested screws to four or more nested screws, that is, as many as is mechanically and electrically feasible. For example, a minimum of two layers can be used and a maximum number of layers can be used that is driven by size limitations. As the number of telescoping nested screws increases, the efficiency of the design will decrease to the losses inherent at the screw thread interfaces. Ultimately, however, any of these designs can be beneficial, depending on the balance of size constraints and power available.

The design is based on the basic screw-drive mechanism where lifting torque is a function of applied axial load (force or pressure), thread pitch, friction parameters, and diameter. In some cases, the equations can be further expanded to capture the full details of thread geometry such as flank and lead angle, and many other special parameters. ACME threads may be generally used to adjust the balance of lifting torque, power required, efficiency, and other functional parameters such as smoothness of operation and cost.

There are no wearable, disposable patch pumps that use this type of mechanism. This is a novel use of basic mechanisms based on wedge design, such as the screw. The novelty of this design is that it brings significant space advantage while trading some mechanical losses. The space savings open up significant design space for novel drug delivery pumps with high delivery accuracy potential. The design of the example embodiments of the present disclosure can be complemented with a ratcheting or indexing drive transmission to further improve the motion resolution, resulting in accurate drug delivery.

The example embodiments described herein employ an elliptical syringe barrel-type reservoir 22 to contain the drug or fluid to be delivered. The elliptical syringe barrel-type reservoir 22 provides anti-rotation functionality and associated benefits. For example, anti-rotation provided by the intrinsic design of an elliptical syringe barrel-type reservoir 22 naturally prevents rotation of the barrel when a torque is applied. The elliptical shape also has the added benefit of potentially saving overall device height. It is, however, possible to employ a separate component to achieve the same anti-rotation. For example, the innermost screw can be keying to a detent or other feature in the stopper assembly 28 or a driver component or surface in a plunger driver assembly 30. Thus, even if the reservoir 22 is not elliptical (e.g., has a round cross-section), anti-rotation of the plunger driver assembly 30 relative to the inner walls of the reservoir 22 during axial translation is still achieved.

Reservoir 22 can be configured to be durable, that is, not removable but rather preinstalled within the fluid delivery device housing 14. The reservoir 22 can be similar in materials to a syringe barrel and associated stopper. The reservoir 33 can be prefilled and the plunger driver assembly 30 initially in a retracted position. Alternatively, the fluid delivery device housing 14 can be provided with a fill port and fluid path 26 from the fill port to the reservoir 22. The fill port can be configured for filling by a user with a syringe, or by using a filling station that fluidically couples to the fill port.

Although various persons, including, but not limited to, a patient or a healthcare professional, can operate or use illustrative embodiments of the present disclosure, for brevity an operator or user will be referred to as a "user" hereinafter.

Although various fluids can be employed in illustrative embodiments of the present disclosure, for brevity the liquid in an injection device will be referred to as "fluid" hereinafter.

It will be understood by one skilled in the art that this disclosure is not limited in its application to the details of construction and the arrangement of components set forth in the above description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The components of the illustrative devices, systems and methods employed in accordance with the illustrated embodiments can be implemented, at least in part, in digital electronic circuitry, analog electronic circuitry, or in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

The above-presented description and figures are intended by way of example only and are not intended to limit the illustrative embodiments in any way except as set forth in the following claims. It is particularly noted that persons skilled in the art can readily combine the various technical aspects of the various elements of the various illustrative embodiments that have been described above in numerous other ways, all of which are considered to be within the scope of the claims.

The invention claimed is:

1. A fluid delivery device comprising:
 a reservoir configured to be preinstalled in a housing of the fluid delivery device and unremoveable therefrom, the reservoir comprising an outlet port at a distal end, and plunger movable along a longitudinal axis of the reservoir, the plunger configured to provide a seal with respect to inner walls of the reservoir to prevent fluid provided in a fluid chamber defined by a first side of the plunger and that comprises the outlet port from leaking into a portion of the reservoir defined by a second side of the plunger; and
 a plunger driver assembly mounted at a proximal end of the reservoir and comprising a plurality of nested, telescoping screws that, when an outermost drive screw is rotated, move from a nested configuration that does not extend into the reservoir to an extended configuration that extends from the proximal end of the reservoir into the reservoir;
 wherein the plurality of nested, telescoping screws comprises an innermost screw that is connected to the plunger and constrained from rotation by an anti-rotation mechanism;
 wherein the reservoir further comprises a gear anchor mounted to its proximal end, the gear anchor comprising an aperture dimensioned to receive a distal end of the outermost drive screw and allow the nested, telescoping screws to extend into the reservoir when the outermost drive screw is rotated; and wherein the gear anchor is disc-shaped and dimensioned to be press fit into the proximal end of the reservoir.

2. The fluid delivery device of claim 1, wherein the reservoir is a syringe barrel-type container.

3. The fluid delivery device of claim 1, wherein the anti-rotation mechanism is the reservoir and plunger having a non-circular cross-section to prevent rotation of the plunger within the reservoir when the outermost drive screw is rotated.

4. The fluid delivery device of claim 3, wherein the reservoir and plunger each have an elliptical cross-section.

5. The fluid delivery device of claim 1, wherein the anti-rotation mechanism comprises a pusher disposed between the plunger and a distal end of the innermost screw, the pusher abutting a proximal side of the plunger and configured to move along the longitudinal axis of the reservoir in response to rotation of the outmost screw.

6. The fluid delivery device of claim 5, wherein the pusher comprises a keying feature that cooperates with a corresponding keying feature on the distal end of the innermost screw to engage the innermost screw with the pusher.

7. The fluid delivery device of claim 6, wherein the keying feature of the pusher comprises a detent, and the corresponding keying feature on the distal end of the innermost screw is dimensioned and/or shaped to be pressure fit into the correspondingly dimensioned and/or shaped detent.

8. The fluid delivery device of claim 7, wherein the detent comprises a through hole to a distal side of the pusher, and the distal end of the innermost screw extends through the through hole.

9. The fluid delivery device of claim 8, wherein the pusher comprises a protrusion on its distal side and the through hole extends through the protrusion.

10. The fluid delivery device of claim 5, wherein the pusher comprises at least one through hole for venting.

11. The fluid delivery device of claim 5, wherein the pusher comprises indents along at least a portion of its perimeter for venting.

12. The fluid delivery device of claim 1, wherein the anti-rotation mechanism comprises a detent on the second side of the plunger dimensioned to cooperate with a distal end of the innermost screw to prevent the plunger from rotating relative to the inner walls of the reservoir when the outermost drive screw is rotated.

13. The fluid delivery device of claim 12, wherein the distal end of the innermost screw is dimensioned and/or shaped to be pressure fit into a correspondingly dimensioned and/or shaped detent.

14. The fluid delivery device of claim 1, wherein the plurality of nested, telescoping screws comprises the outermost drive screw having an inner diameter and inner threads dimensioned to receive a sleeve screw having external threads configured to cooperate with the inner threads to advance the sleeve screw within the outermost drive screw when the outermost drive screw is rotated.

15. The fluid delivery device of claim 14, wherein the sleeve screw has an inner diameter and inner threads dimensioned to receive the innermost screw, the innermost screw having external threads configured to cooperate with the inner threads of the sleeve screw to advance the innermost screw within the sleeve screw when the sleeve screw is rotated.

16. The fluid delivery device of claim 1, wherein the plurality of nested, telescoping screws have right handed threads, and respective inner screw parameters and outer screw parameters that employ the same pitch.

17. The fluid delivery device of claim 1, wherein the plurality of nested, telescoping screws have left handed threads, and respective inner screw parameters and outer screw parameters that employ the same pitch.

18. The fluid delivery device of claim 1, wherein the gear anchor comprises a through hole for venting.

19. The fluid delivery device of claim 1, wherein the aperture in the gear anchor is configured to provide stable support for the outermost drive screw while allowing the outermost drive screw to be rotated relative to the gear anchor.

20. The fluid delivery device of claim 1, wherein, when the plunger driver assembly is in its nested configuration, a distal end of the innermost screw is flush with respect to a distal side of the gear anchor.

21. The fluid delivery device of claim 1, wherein, when the plunger driver assembly is in its nested configuration, the distal end of the innermost screw protrudes from a distal side of the gear anchor a designated length corresponding to a depth of a detent provided on either of the second side of the plunger or an intermediate pusher between the plunger and the distal end of the innermost screw.

22. The fluid delivery device of claim 1, further comprising a thrust bearing feature provided relative to the plunger driver assembly and a support structure of the plunger driver assembly to minimize axial thrust load from the telescoping screws.

23. The fluid delivery device of claim 22, wherein the thrust bearing feature comprises a cap disposed on the outermost drive screw, the cap having a boss for contacting a portion of the support structure to resist an axial thrust load directed toward the proximal end of the plunger driver assembly and generated by the plunger driver assembly, plunger or fluid in the fluid chamber.

24. The fluid delivery device of claim 1, further comprising an encoder provided relative to the plunger driver assembly to generate feedback data related to operation of the plunger driver assembly.

25. The fluid delivery device of claim 1, wherein the anti-rotation mechanism is disposed at a distal end of the innermost screw.

26. A fluid delivery device comprising:
a reservoir comprising an outlet port at a distal end, and plunger movable along a longitudinal axis of the reservoir, the plunger configured to provide a seal with respect to inner walls of the reservoir to prevent fluid provided in a fluid chamber defined by a first side of the plunger and that comprises the outlet port from leaking into a portion of the reservoir defined by a second side of the plunger;
a plunger driver assembly mounted at a proximal end of the reservoir and comprising a plurality of nested, telescoping screws that, when an outermost drive screw is rotated, move from a nested configuration that does not extend into the reservoir to an extended configuration that extends from the proximal end of the reservoir into the reservoir;
wherein the plurality of nested, telescoping screws comprises an innermost screw that is connected to the plunger and constrained from rotation by an anti-rotation mechanism;
wherein the anti-rotation mechanism comprises a pusher disposed between the plunger and a distal end of the innermost screw, the pusher abutting a proximal side of the plunger and configured to move along the longitudinal axis of the reservoir in response to rotation of the outmost screw;

wherein the pusher comprises a keying feature that cooperates with a corresponding keying feature on the distal end of the innermost screw to engage the innermost screw with the pusher;

wherein the keying feature of the pusher comprises a detent, and the corresponding keying feature on the distal end of the innermost screw is dimensioned and/or shaped to be pressure fit into the correspondingly dimensioned and/or shaped detent;

wherein the detent comprises a through hole to a distal side of the pusher, and the distal end of the innermost screw extends through the through hole; and wherein the distal end of the innermost screw is heat staked at the distal side of the pusher at the through hole.

27. The fluid delivery device of claim 26, wherein the through hole comprises anti-rotation slots.

28. A fluid delivery device comprising:
a reservoir comprising an outlet port at a distal end, and plunger movable along a longitudinal axis of the reservoir, the plunger configured to provide a seal with respect to inner walls of the reservoir to prevent fluid provided in a fluid chamber defined by a first side of the plunger and that comprises the outlet port from leaking into a portion of the reservoir defined by a second side of the plunger;
a plunger driver assembly mounted at a proximal end of the reservoir and comprising a plurality of nested, telescoping screws that, when an outermost drive screw is rotated, move from a nested configuration that does not extend into the reservoir to an extended configuration that extends from the proximal end of the reservoir into the reservoir;
wherein the plurality of nested, telescoping screws comprises an innermost screw that is connected to the plunger and constrained from rotation by an anti-rotation mechanism;
wherein the plurality of nested, telescoping screws comprises the outermost drive screw having an inner diameter and inner threads dimensioned to receive a sleeve screw having external threads configured to cooperate with the inner threads to advance the sleeve screw within the outermost drive screw when the outermost drive screw is rotated;
wherein the sleeve screw has an inner diameter and inner threads dimensioned to receive the innermost screw, the innermost screw having external threads configured to cooperate with the inner threads of the sleeve screw to advance the innermost screw within the sleeve screw when the sleeve screw is rotate; and
wherein a torque ratio of the innermost screw is less that a torque ratio of the sleeve screw, and the torque ratio of the sleeve screw is less that a torque ratio of the outermost drive screw to allow the innermost screw, when constrained in rotation, to extend along the sleeve screw into the reservoir before the sleeve screw commences rotating relative to the outermost drive screw and advancing into the reservoir.

* * * * *